(12) United States Patent
Kindel et al.

(10) Patent No.: US 8,574,554 B2
(45) Date of Patent: Nov. 5, 2013

(54) USES OF 4-METHYL-5-HYDROXY-HEXANOIC ACID LACTONE

(75) Inventors: Günter Kindel, Höxter (DE); Bernd Wiedwald, Holzminden (DE); Axel Schöning, Holzminden (DE); Ingo Wöhrle, Holzminden (DE); Hubert Loges, Höxter (DE); Rita Lages, Bodenwerder (DE)

(73) Assignee: Symrise AG, Holzminden (DE)

( * ) Notice: Subject to any disclaimer, the term of this patent is extended or adjusted under 35 U.S.C. 154(b) by 477 days.

(21) Appl. No.: 11/736,894

(22) Filed: Apr. 18, 2007

(65) Prior Publication Data
US 2007/0254826 A1 Nov. 1, 2007

Related U.S. Application Data

(60) Provisional application No. 60/792,945, filed on Apr. 19, 2006.

(51) Int. Cl.
*A61K 8/00* (2006.01)
*A61K 8/18* (2006.01)
*A61Q 11/00* (2006.01)

(52) U.S. Cl.
USPC ........................................... 424/49

(58) Field of Classification Search
USPC ............................................ 424/49
See application file for complete search history.

(56) References Cited

U.S. PATENT DOCUMENTS

| 4,288,350 | A |   | 9/1981 | Nieuwland |            |
|-----------|---|---|--------|-----------|------------|
| 4,822,621 | A | * | 4/1989 | Glass et al. | 426/5    |
| 5,248,792 | A | * | 9/1993 | Kaiser    | 549/273    |

FOREIGN PATENT DOCUMENTS

| EP | 0513627 | 11/1992 |
| JP | 60072816 | 4/1985 |

OTHER PUBLICATIONS

Abraham et al (J. Argic. Food Chem. (1994); 42:2344-2348).*
MedicineNet.com (Taste and Smell. http://www.medicinenet.com/script/main/art.asp?articlekey=212; Oct. 24, 2002).*
Database FSTA[Online] Intrnational Food Information Service (IFIS), Frankfurt-main, DE: XP002448569.

* cited by examiner

*Primary Examiner* — Allison M. Ford
*Assistant Examiner* — Chris Simmons
(74) *Attorney, Agent, or Firm* — Ryan A. Schneider, Esq.; Troy S. Kleckley; Troutman Sanders LLP

(57) ABSTRACT

The present invention relates to the use of 4-methyl-delta-hexylactone for imparting, modifying and/or intensifying one or more smell or flavor impressions from the group consisting of hay, coumarin, lactone and richness in the mouth.

14 Claims, No Drawings

USES OF 4-METHYL-5-HYDROXY-HEXANOIC ACID LACTONE

CROSS REFERENCE TO RELATED APPLICATIONS

This application claims the benefit of U.S. Provisional Application 60/792,945, filed Apr. 19, 2006.

FIELD OF THE INVENTION

The present invention primarily relates to the use of 4-methyl-delta-hexylactone (4-methyl-5-hydroxy-hexanoic acid lactone or 5,6-dimethyltetrahydro-2H-pyran-2-one) for imparting, modifying and/or intensifying certain smell or flavour impressions, and in addition certain perfumed or aromatized articles, such as odoriferous and aroma substance mixtures (odoriferous and aroma substance compositions) comprising (a) a (sensorially active) amount of 4-methyl-delta-hexylactone, (b) one, several or all of the compounds chosen from the group consisting of (i) menthol, (ii) (−)-carvone, (iii) menthone and (iv) isomenthone, and, preferably, (c) nonenolide. The invention furthermore relates to certain formulations and methods for imparting, modifying and/or intensifying certain smell or flavour impressions and for the preparation of odoriferous or aroma substance compositions which comprise 4-methyl-delta-hexylactone.

BACKGROUND OF THE INVENTION

In spite of a large number of already existing odoriferous and aroma substances, in the perfume and aroma industry there also continues to be a general demand for novel odoriferous and aroma substances which have, beyond their primary, namely intrinsic smell and flavour properties, additional positive secondary properties, for example in mixtures with other odoriferous and aroma substances.

There is thus a demand for odoriferous and aroma substances which (in odoriferous or aroma substance compositions) generate interesting smell notes and with their novel and original fragrance and flavour properties extend the possibilities of the perfumer or flavourist.

For creation of novel modern compositions, there is a constant demand for odoriferous and aroma substances having particular smell/flavour properties which are suitable for serving as a constituent of a composition of novel perfumes or aromas having a complex smell or flavour character. Thus, in particular, odoriferous and aroma substances are sought which, alongside a hay-like fragrance or flavour note, have further notes and aspects which impart to them smell or flavour character and complexity.

SUMMARY OF THE INVENTION

The object on which this invention was based was therefore substantially to discover odoriferous and aroma substances having hay-like (primary or secondary) notes which are paired with further interesting and original smell or flavour properties, as a result of which the odoriferous and aroma substances sought render possible novel and original odoriferous and aroma substance compositions having particular notes and aspects.

DETAILED DESCRIPTION OF THE INVENTION

According to the invention, this object is primarily achieved by the use of 4-methyl-delta-hexylactone as an odoriferous and/or aroma substance for imparting, modifying and/or intensifying one or more smell or flavour impressions from the group consisting of hay (of dry grass and somewhat sweetish), coumarin, lactone and richness in the mouth. Further aspects of the invention emerge from the attached patent claims and the following description and in this context relate in particular to perfumed or aromatized articles (in particular odoriferous or aroma substance compositions, and formulations for nutrition, oral care or consumption for pleasure) as well as methods.

The invention is based, inter alia, on the surprising finding that 4-methyl-delta-hexylactone is suitable as an odoriferous and aroma substance having a hay-like note.

The structural formula of 4-methyl-5-hydroxy-hexanoic acid lactone (5,6-dimethyltetrahydro-2H-pyran-2-one, 4-methyl-delta-hexylactone) is represented below by formula A:

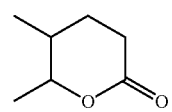

A

In this context, 4-methyl-delta-hexylactone of the formula A can be in the syn or anti configuration, in the form of the enantiomer of (R,R) configuration, enantiomer of (R,S) configuration, enantiomer of (S,R) configuration, enantiomer of (S,S) configuration or in the form of any desired mixture of the enantiomers, in particular in the form of the racemate, or also in the form of any desired mixture of the corresponding diastereomers.

The compound of the formula A is known and has been found, for example, in seeds of fenugreek (Planta Medica 1985, 533-534) and in tobacco leaves dried in hot air (flue-cured tobacco), see, for example, Tobacco Science 1976, 20, 125-133 or also J. Chromatogr. A 2004, 1040, 1-17. According to Tobacco Science 1976, 20, 125-133, the compound of the formula A has a sweet, phenolic and chemical flavour in tobacco smoke. Tobacco-containing products are not preferred products in the context of the present invention.

According to J. Agric. Food Chem. 1994, 42, 2344-2348, the compound of the formula A has been found in some volatile fractions of certain fungus cultures (Basidiomycetes). The smell of 4-methyl-delta-hexylactone determined by GC/olfactometry has been described as fruity.

In the recently published article Flavour & Fragrance Journal 2006, 21, 193-197, the following descriptions of smell are given for 5-methyl-delta-lactones, which were found in the lactone fraction of a commercially obtainable liquorice extract (*Glycyrrhia glabra* L.):

5-methyl-5-heptanolide: hay, coumarin, stable, animal and herbal;

5-methyl-5-octanolide: foul water, phenolic, woody, fruity and fungal;

5-methyl-5-nonanolide: lactonic, dried herbs, hay, fruity, sweet and coconut;

5-methyl-5-decanolide: foul water, slightly lactonic, herbal, woody, and milky.

EP 0 513 627 describes the delta-lactones 4-methyl-5-octanolide to 4-methyl-5-tridecanolide generally as odoriferous and flavour substances. Thus, 5-methyl-6-pentyl-tetrahydro-alpha-pyrone (4-methyl-5-decanolide) is described as an odoriferous substances having a smell reminiscent of certain blossom fragrances and at the same time of caramel, condensed milk and coconut, in particular coconut milk. According to EP 0 513 627, 4-methyl-5-nonanolide has a smell of coconut and celery.

According to JP 60-72816 A, the compound of the formula A can be employed as a medicament for treatment of sleep disorders or of psychoneurotic diseases. The preparation of the compound A is also described in this document.

According to EP 0 513 627, the compound of the formula A can also be prepared by Bayer-Villiger oxidation with per-acids, such as, for example, peracetic acid, from 2,3-dimethylcyclopentanone, which in turn is obtainable by hydrogenation from 2,3-dimethylcyclopentenone.

Coumarin (2H-1-benzopyran-2-one) is the essential constituent of the smell and flavour of woodruff (*Asperula odorata, Galium odoratum*). Coumarin has, inter alia, a hay-like note and was a frequently used odoriferous and aroma substance in particular in earlier times. However, coumarin leads to impairment of health, in particular in higher doses; for toxicological reasons it would therefore be desirable to find an alternative compound for coumarin.

The fact that the 4-methyl-delta-hexylactone to be employed according to the invention is capable of causing a hay-like, coumarinic smell and flavour is surprising. In this context it is to be mentioned that the hay-like note of 4-methyl-delta-hexylactone is noticeably more pronounced than the coumarinic aspect.

4-Methyl-delta-hexylactone is capable, in particular in combination with one (i.e. an individual one of the compounds (i), (ii), (iii) or (iv) listed in the following), several or all of the compounds chosen from the group consisting of (i) menthol, (ii) (−)-carvone, (iii) menthone and (iv) isomenthone, depending on the use concentration, of causing a diverse smell and flavour impression of the notes hay, coumarin, lactone and/or richness in the mouth.

On the basis of the smell and flavour impressions imparted by it, 4-methyl-delta-hexylactone of the formula A can be employed in particular in the preparation of aromas and oils which are extremely similar in their sensory (smell and/or flavour) properties and preferably in their consistency to natural peppermint and/or spearmint aromas or peppermint and/or spearmint oils. In this connection, sensory reconstitution, recomposition or reconstruction of the natural aromas or oils are referred to.

The (sensory) reconstitution (recomposition, reconstruction) of a natural peppermint and/or spearmint oil is of interest, for example, because, in contrast to their natural prototypes, which are essential oils obtained by means of steam distillation, such (sensorially) reconstituted, recomposed or reconstructed oils are not subject to any variations in (sensory) quality and do not depend in their (sensory) properties on the harvest, the cultivation area and/or the process by which they are obtained.

In addition to the 4-methyl-delta-hexylactone of the formula A, the gamma-lactone nonenolide (2-nonen-4-olide; 4-hydroxy-2-nonenoic acid lactone, 5-pentyl-5H-furan-2-one) of the formula C is also preferably employed in the reconstitution, recomposition or reconstruction of natural peppermint and/or spearmint aromas and natural peppermint and/or spearmint oils, in this context see below in detail.

C

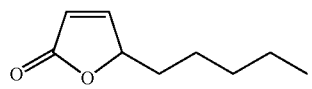

According to a preferred embodiment of the use according to the invention, 4-methyl-delta-hexylactone (preferably together with nonenolide of the formula C) is employed for imparting, modifying and/or intensifying one or more smell or flavour impressions from the group consisting of hay and coumarin, wherein the resulting product (article) containing 4-methyl-delta-hexylactone does not contain the compound coumarin itself and preferably also does not contain any fraction of a natural oil or aroma which itself has a hay-like, coumarinic note.

Natural peppermint oils which can be reconstituted (sensorially) using 4-methyl-delta-hexylactone are understood as meaning specifically the essential (i.e. obtained by means of steam distillation) oils of certain *Mentha* species, in particular from *Mentha arvensis* (field mint, also called cornmint in U.S. language) and from *Mentha piperita* (called peppermint in US language), which include *Mentha piperita* oils with names of regional origin from specific cultivation areas, such as Willamette, Yakima and Madras.

The said natural peppermint oils have a hay-like, coumarinic note which is absent from the (sensorially) reconstituted, recomposed or reconstructed peppermint oils known hitherto. The hay-like, coumarinic note of natural peppermint oils, nevertheless, is based not on coumarin, since these do not contain coumarin, but without doubt on other compounds which in some cases are unidentified and are present in peppermint oils only in traces.

Natural spearmint oils which can be reconstituted (sensorially) using 4-methyl-delta-hexylactone are understood as meaning specifically the essential oils from *Mentha cardiaca* or *Mentha spicata*.

The invention furthermore relates to perfumed or aromatized articles comprising or consisting of (a) 4-methyl-delta-hexylactone, (b) one, several or all of the compounds chosen from the group consisting of (i) menthol, (ii) (−)-carvone, (iii) menthone, (iv) isomenthone, and, preferably, (c) nonenolide and/or (d) menthyl acetate.

4-Methyl-delta-hexylactone imparts a particular naturalness and/or authenticity to a correspondingly perfumed or aromatized article.

In this context, a perfumed or aromatized article according to the invention is chosen from the group consisting of:
 odoriferous or aroma substance composition, preferably peppermint or spearmint aroma substance composition,
 formulation for nutrition, preferably foodstuff which is ready-to-consume or not ready-to-consume,
 formulation for oral care and
 formulation for consumption for pleasure.

The perfumed or aromatized articles, in particular the preferred articles according to the invention from the abovementioned group, preferably comprise an amount of 4-methyl-delta-hexylactone which is sufficient to impart, to modify and/or to intensify one or more smell or flavour impressions from the group consisting of hay, coumarin, lactone and richness in the mouth. Preferably, the articles according to the invention comprise no coumarin and no fraction of a natural oil or aroma which itself has a hay-like, coumarinic note.

l-Menthol has a unique refreshing flavour, a minty smell and a potent cooling effect on skin and mucous membrane. It is used, for example, in oral care, in cosmetic and pharmaceutical preparations, in tobacco and in confectionery, as described e.g. in Perfumer&Flavorist, vol. 13, October-November 1988, p. 37. l-Menthol is the main constituent of peppermint oils from *Mentha arvensis* (content: about 70-80 wt. %) and *Mentha piperita* (content: about 50-80 wt. %).

In the context of the invention, the menthol preferably employed in articles according to the invention can be d-menthol, l-menthol or any desired mixture thereof, l-menthol, d-menthol and racemic menthol being preferred and l-menthol being particularly preferred since l-menthol has the abovementioned sensory properties which are very advantageous for (sensory) reconstitution of peppermint oils.

Any desired mixtures of synthetic and natural menthol and of racemic and enantiomerically pure menthol can also be employed.

The menthol preferably employed according to the invention can be of synthetic or natural origin, but the use of synthetic menthol is preferred.

(−)-Carvone is the main constituent of spearmint oil (content: about 70-80 wt. %) and has a herbal, spearmint-like smell and flavour. In this context, the (−)-carvone preferably employed according to the invention can be of synthetic or natural origin.

Menthone and isomenthone (both can be independently of one another in the form of the (+) and/or (−) enantiomer) occur in many essential oils, and peppermint oils of *Mentha* species can even contain them in an amount of more than 50 wt. %. Menthone has a typical strong minty smell and flavour and has a cooling effect, isomenthone is minty, camphorous and cooling, and somewhat more muffled here than menthone.

In the context of the invention, the menthone preferably employed can be (+)-menthone, (−)-menthone and any desired mixture thereof, (+)-menthone, (−)-menthone and racemic menthone being preferred and (−)-menthone being particularly preferred since this is very advantageous for the preparation of non-natural or synthetic peppermint oils or aromas and the (sensory) reconstitution of natural peppermint oils.

In the context of the invention, the isomenthone employed can be (+)-isomenthone, (−)-isomenthone and any desired mixture thereof, (+)-isomenthone, (−)-isomenthone and racemic isomenthone being preferred and (+)-isomenthone being particularly preferred since this is very advantageous for the preparation of non-natural or synthetic peppermint oils or aromas and the (sensory) reconstitution of natural peppermint oils.

From that stated above, it emerges that the 4-methyl-delta-hexylactone to be employed according to the invention is capable in particular of imparting, modifying and/or intensifying the smell or flavour impressions mentioned when it is present in mixtures with one, several or all of the compounds chosen from the group consisting of (i) menthol, (ii) (−)-carvone, (iii) menthone and (iv) isomenthone. 4-Methyl-delta-hexylactone is therefore particularly suitable for incorporation into odoriferous or aroma substance compositions, preferably peppermint/or spearmint aroma compositions, and into formulations for nutrition, oral care or consumption for pleasure which have peppermint or spearmint smell or flavour notes.

This usability of 4-methyl-delta-hexylactone is remarkable in particular because not only are the known smell and flavour impressions thereof mentioned above (sweet, phenolic, chemical; fruity; in this respect see the above documents) largely or completely suppressed in combination with one, several or all of the compounds from the group consisting of (i) menthol, (ii) (−)-carvone, (iii) menthone and (iv) isomenthone, but instead the desired hay-like or coumarinic note sought occurs. Furthermore, 4-methyl-delta-hexylactone has a low sensory threshold value, so that it is already perceptible in a very low dosage and, when incorporated into an odoriferous or aroma substance composition, can influence this significantly (in this context see also the statements below).

The following Table 1 illustrates the sensory effects observed in respect of a hay-like or coumarinic note in mixture of one or more substances from the group consisting of (i) menthol, (ii) (−)-carvone, (iii) menthone and (iv) isomenthone and 4-methyl-delta-hexylactone of the formula A. Aromas T1 to T6 according to the invention in Table 1 were tasted at a dosage in each case of 0.2 wt. % in a 5 wt. % strength aqueous sugar solution (sucrose solution).

TABLE 1

(all contents are stated in wt. %)

| | T1 | T2 | T3 | T4 | T5 | T6 |
|---|---|---|---|---|---|---|
| 4-Methyl-delta-hexalactone of the formula A | 0.10 | 0.20 | 0.15 | 0.1 | 0.15 | 0.1 |
| (i) Menthol | 99.9 | | | 50.0 | 50.0 | 65.0 |
| (ii) (−)-Carvone | | 99.8 | | 49.9 | | |
| (iii) Menthone | | | 99.85 | | 25.0 | 23.0 |
| (iv) Isomenthone | | | | | 24.85 | 11.8 |
| (c) Nonenolide | | | | | | 0.1 |
| Evaluation of the hay and coumarin notes | + | + | + | ++ | +++ | ++++ |

+: noticeable hay-like or coumarinic note;
++: moderate hay-like or coumarinic note;
+++: pronounced hay-like or coumarinic note;
++++: strong hay-like or coumarinic note.

The results shown in Table 1 demonstrate that a hay-like or coumarinic note already occurs in mixtures of 4-methyl-delta-hexylactone of the formula A and an individual substance from the group consisting of (i) menthol, (ii) (−)-carvone, (iii) menthone and (iv) isomenthone. A hay-like or coumarinic note occurs more significantly when two or more substances from the group consisting of (i) menthol, (ii) (−)-carvone, (iii) menthone and (iv) isomenthone are combined with 4-methyl-delta-hexylactone of the formula A, it furthermore being possible also to observe a rounding-off of the smell or flavour profile.

For the 4-methyl-delta-hexylactone to be employed according to the invention, the following flavour properties were found in the tasting of a mixture consisting of 5 wt. % strength aqueous sugar solution and peppermint aroma (dosage: 5,000 ppm=0.5 wt. %, the peppermint aroma contained (i) l-menthol to the extent of 62 wt. %, 5% menthyl acetate (constituent d)) and in total (iii) (−)-menthone and (iv) (+)-isomenthone to the extent of 23 wt. %, and further constituents which make no substantial contribution to the flavour impression):

at a concentration of 4-methyl-delta-hexylactone of 15 ppm (based on the total amount of the mixture tasted):
the hay and coumarin notes imparted when non-natural peppermint oil is employed (analogously, when natural peppermint oil was used, e.g. with a content of l-menthol of 70 wt. %, the hay and coumarin notes were intensified).

This effect dominates in the range of about 5-20 ppm.

At a concentration of 4-methyl-delta-hexylactone of 25 ppm: lactone note This effect dominates in the range of about 20-30 ppm.

At a concentration of 4-methyl-delta-hexylactone of 40 ppm: richness in the mouth This effect dominates above 30 ppm, i.e. in the range of about 30-100 ppm.

At an even higher dosage, for example in the region of 1 wt. % and higher, based on the aroma composition, fruity notes occur more intensely.

The abovementioned smell and flavour effects in each case merge into one another in the boundary ranges of the concentrations stated. Concentration ranges in which the particular smell or flavour effect stated clearly dominates have been given above.

In the present context, the flavour impression "richness in the mouth" is understood as meaning the flavour impression of smoothness, creaminess and butteriness imparting a rich sensation in the mouth.

The 4-methyl-delta-hexylactone of the formula A to be employed according to the invention can also be employed for reducing the bitterness of bitter-tasting substances. When 4-methyl-delta-hexylactone was employed in articles which have a bitter flavour note, in some cases a reduction in the bitterness was already found on addition of small amounts of 4-methyl-delta-hexylactone of the formula A, for example in chewing gums in which the chewing gum base was found to be bitter-tasting, or certain sweetener-containing articles which are evaluated overall as bitter-tasting because of the presence of certain sweeteners having a bitter after-taste. A reduction in the bitterness was likewise to be found in the preparation of certain perfumed or aromatized articles according to the invention which contained menthol, which has a bitter taste at a higher concentration. The presence of 4-methyl-delta-hexylactone alongside menthol suppressed the bitter-tasting action thereof.

Odoriferous or aroma substance compositions according to the invention preferably comprise an amount of 4-methyl-delta-hexylactone of the formula A in the range of from 50 to 8,000 ppm, preferably 100 to 5,000 ppm and particularly preferably 250 to 2,000 ppm, based on the total amount of the odoriferous or aroma substance composition.

Preferably, the weight ratio of 4-methyl-delta-hexylactone of the formula A to the total weight of the compounds of the group consisting of (i) menthol, (ii) (−)-carvone, (iii) menthone and (iv) isomenthone is less than 1:1, and the weight ratio is preferably in the range of from 1:50 to 1:2500, particularly preferably in the range of from 1:100 to 1:1200.

Odoriferous or aroma substance compositions according to the invention or formulations according to the invention for nutrition, oral care or consumption for pleasure (in particular according to one of the embodiments described as preferred above) which are preferred are those which comprise an amount of one or more compounds chosen from the group consisting of (i) menthol, (ii) (−)-carvone, (iii) menthone and (iv) isomenthone which is sufficient to generate a dominant peppermint and/or spearmint smell or flavour note in the odoriferous or aroma substance composition or the formulation. Such odoriferous or aroma substance compositions or such formulations—as stated—comprise an amount of 4-methyl-delta-hexylactone which is sufficient to impart, to modify and/or to intensify one or more smell or flavour impressions from the group consisting of hay, coumarin, lactone and richness in the mouth. The substance coumarin is preferably not present in such an article according to the invention, and such an article preferably also contains no natural peppermint or spearmint oil and no natural peppermint or spearmint aroma. In particular, however, preferably at least no fraction of a natural oil or aroma such as is responsible for the hay-like, coumarinic note in the said natural oils or aromas is present.

In preferred odoriferous or aroma substance compositions according to the invention, the concentrations of the relevant abovementioned constituents are preferably within certain ranges. Particularly preferred odoriferous or aroma substance compositions according to the invention (preferably according to one of the abovementioned preferred embodiments) are those comprising:

(a) 4-methyl-delta-hexylactone in an amount of from preferably 50 to 8,000 ppm, preferably 100 to 5,000 ppm and particularly preferably 250 to 2,000 ppm, and (b) (i) menthol, preferably l-menthol, in an amount of from 1 to 80 wt. %, preferably 5 to 70 wt. %, and/or (ii) (−)-carvone in an amount of from 1 to 80 wt. %, preferably 5 to 80 wt. %, and/or (iii) menthone, preferably (−)-menthone, and/or (iv) isomenthone, preferably (+)-isomenthone, in a total amount of from 0.5 to 60 wt. %, preferably 1 to 50 wt. %, and, preferably, (c) nonenolide in an amount of from 50 to 8,000 ppm, preferably 100 to 5,000 ppm and particularly preferably 250 to 2,000 ppm, and/or (d) menthyl acetate, preferably (−)-menthyl acetate, in an amount of from 1 to 20 wt. %, preferably 2 to 12 wt. %, particularly preferably 3 to 10 wt. %, where the amounts stated are in each case based on the total amount of the odoriferous or aroma substance composition.

The content of (i) menthol here in the reconstituted (recombined, reconstructed) peppermint aromas and peppermint oils is preferably in the range of from 30 to 60 wt. %.

The content of (−)-carvone here in the reconstituted (recombined, reconstructed) spearmint aromas and spearmint oils is preferably in the range of from 30 to 70 wt. %.

The total content of menthone and isomenthone here in the reconstituted (recombined, reconstructed) peppermint aromas and peppermint oils is preferably in the range of from 5 to 40 wt. %.

The structural formulae of the particularly preferred compounds of group (b) are shown in the following:

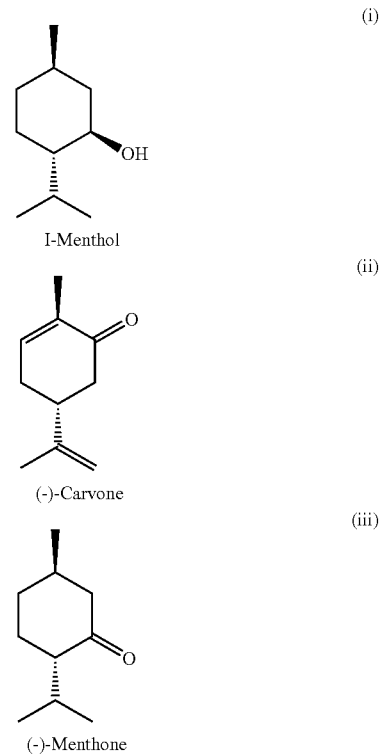

(iv)

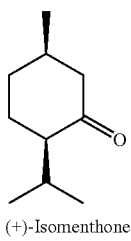

(+)-Isomenthone

The structural formula of the (−)-menthyl acetate (l-menthyl acetate) which is particularly preferably to be employed according to the invention as component (d) is represented in the following formula D.

D

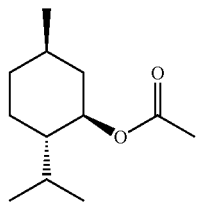

The preferred component (d) (−)-menthyl acetate (of the formula D) has a fresh-fruity, pepperminty smell and completes the smell and aroma profile in particular in reconstituted (recombined, reconstructed) peppermint aromas and peppermint oils.

Certain concentrations of 4-methyl-delta-hexylactone or the odoriferous or aroma substance compositions according to the invention are also preferred in the formulations according to the invention for nutrition, oral care or consumption for pleasure (as stated above). Formulations according to the invention which are particularly preferred are those comprising 4-methyl-delta-hexylactone in an amount in the range of from 0.05 to 80 ppm, preferably in the range of from 0.1 to 50 ppm and particularly preferably in the range of from 0.25 to 20 ppm or an odoriferous or aroma substance composition according to the invention (preferably in a preferred embodiment) in an amount of from 0.05 to (in certain cases) 50 wt. %, preferably in the range of from 0.05 to 6 wt. %, preferably in the range of from 0.1 to 3 wt. %, based on the total weight of the formulation.

The concentrations stated above for formulations according to the invention relate in particular to ready-to-use formulations, i.e. formulations which can be employed directly by the end user. Ready-to-use formulations are, in particular, ready-to-consume foodstuffs, such as e.g. ready-to-consume confectionery or ready-to-consume drinks. However, ready-to-use formulations are also oral care products (oral hygiene products) which can be employed directly by the consumer.

In ready-to-use formulations, in particular in confectionery (such as chewing gums and caramels) or in oral hygiene products (such as toothpastes and dental creams and gels), the content of an odoriferous or aroma substance composition according to the invention comprising 4-methyl-delta-hexylactone of the formula A is preferably in the range of from 0.05 to 6 wt. %, preferably in the range of from 0.1 to 3 wt. %, based on the total weight of the ready-to-use formulation.

In ready-to-consume alcoholic or non-alcoholic drinks in the context of the invention, the content of an odoriferous or aroma substance composition according to the invention comprising 4-methyl-delta-hexylactone of the formula A is preferably in the range of from 3 to 100 ppm, preferably in the range of from 5 to 50 ppm, based on the total weight of the ready-to-consume formulation.

Needless to say, if the ready-to-use formulation is a capsule suitable for direct consumption (see Example F10 below), the content of odoriferous or aroma substance composition according to the invention comprising 4-methyl-delta-hexylactone to be employed can be significantly higher and can be up to 50 wt. %.

The formulations according to the invention for nutrition, oral care or consumption for pleasure are regularly products which are intended to be introduced into the human oral cavity, to remain there for a certain period of time and then either to be consumed (e.g. ready-to-consume foodstuffs) or to be removed from the oral cavity again (e.g. chewing gums or toothpaste). It goes without saying that the use of 4-methyl-delta-hexylactone or the odoriferous or aroma substance compositions according to the invention is envisaged for any type of such products. In this context, these products include all substances or products which are intended to be taken in by humans in the processed, partly processed or non-processed state. These also include substances which are added to foodstuffs during their production, processing or preparation and are envisaged for introduction into the human oral cavity.

It goes without saying that 4-methyl-delta-hexylactone and the odoriferous or aroma substance compositions according to the invention can be employed in particular in foodstuffs. In the context of the present text, a "foodstuff" is understood as meaning in particular substances which are intended to be swallowed in the unchanged, prepared or processed state by humans and then digested; in this respect, coatings, coverings or other wrappings which are intended also to be swallowed or for which swallowing is to be foreseen are also understood as foodstuffs. Certain products which are conventionally removed again from the oral cavity (e.g. chewing gums) are also to be understood as foodstuffs in the context of the present text, since it cannot be ruled out that they will be at least partly swallowed.

In particular, 4-methyl-delta-hexylactone or an odoriferous or aroma substance composition according to the invention is employed in ready-to-consume foodstuffs. A ready-to-consume foodstuff is understood here as meaning a foodstuff which is already complete in its composition in respect of the substances which are decisive for the flavour. The term "ready-to-consume foodstuffs" also includes drinks and solid or semi-solid ready-to-consume foodstuffs. Examples which may be mentioned are deep-frozen products which must be thawed and heated to the consumption temperature before consumption. Ready-to-consume foodstuffs also include products such as yogurt or ice-cream, and also chewing gums or hard caramels.

4-Methyl-delta-hexylactone and odoriferous or aroma substance compositions according to the invention can also be employed in semi-finished foodstuff goods. The term semi-finished foodstuff goods here relates to foodstuffs which are intended to be consumed only in the further processed state, after addition of aroma or flavour substances which are (co)decisive for the sensory impression.

An oral care product (also called oral hygiene product or oral hygiene formulation) in the context of the invention is understood as meaning one of the formulations familiar to the person skilled in the art for cleansing and care of the oral cavity and the pharyngeal cavity and for refreshing the breath.

This expressly includes care of the teeth and gums. Presentation forms of the usual oral hygiene formulations are creams, gels, pastes, foams, emulsions, suspensions, aerosols and sprays, and also capsules, granules, pastilles, tablets, bonbons or chewing gums, without this list being intended to be understood as limiting for the purpose of this invention.

Preferred ready-to-consume alcoholic or non-alcoholic drinks in the context of the invention are (preferably non-carbonated) non-alcoholic refreshing drinks or alcoholic liqueurs.

In a ready-to-consume non-alcoholic drink in the context of the invention, the content of an odoriferous or aroma substance composition according to the invention comprising 4-methyl-delta-hexylactone of the formula A is preferably in the range of from 3 to 30 ppm (corresponding to about 0.3 to 3 g per 100 liters of drink), preferably in the range of from 5 to 15 ppm (corresponding to about 0.5 to 1.5 g per 100 liters of drink), based on the total weight of the ready-to-consume formulation. Ready-to-consume non-alcoholic drinks in the context of the invention preferably have a sugar content (sucrose content) or a content of glucose syrup in the range of from 8 to 15 wt. %, preferably in the range of from 9 to 13 wt. %, based on the ready-to-consume non-alcoholic drink.

In a ready-to-consume alcoholic drink in the context of the invention, the content of an odoriferous or aroma substance composition according to the invention comprising 4-methyl-delta-hexylactone of the formula A is preferably in the range of from 10 to 100 ppm (corresponding to about 1 to 10 g per 100 liters of drink), preferably in the range of from 25 to 80 ppm (corresponding to about 2.5 to 8 g per 100 liters of drink), based on the total weight of the ready-to-consume formulation. Ready-to-consume drinks in the context of the invention are preferably liqueurs and preferably have a sugar content (sucrose content) or a content of glucose syrup in the range of from 10 to 25 wt. %, preferably in the range of from 15 to 20 wt. %, based on the ready-to-consume alcoholic drink. In this context, the alcohol content is preferably in the range of from 12 to 25 vol. %, preferably in the range of from 15 to 20 vol. %, based on the ready-to-consume alcoholic drink.

A preferred ready-to-use formulation according to the invention is (A) ready-to-consume and in this context sugar-free, reduced-sugar or sugar-containing confectionery, in particular in the form of a chocolate, filled chocolate (for example with an aromatized fondant mass, e.g. of the After-Eight type), chocolate bar product, fruit gum, hard or soft caramel, bonbon for chewing, sugar bead, lollypop, capsule (preferably seamless capsule, preferably for direct consumption, preferably having a casing based on gelatine and/or alginate), chewing gum (e.g. in the form of strips, compressed tablets, pellets, pads, balls, hollow balls), (B) an oral care product (oral hygiene product), in particular in the form of a toothpaste, dental cream, dental gel, dental powder, tooth-cleaning liquid, tooth-cleaning foam, mouthwash, dental cream and mouthwash as a 2-in-1 product, bonbon for sucking, oral spray, dental floss or dental care chewing gum, or (C) an alcoholic or alcohol-free drink.

The terms "formulation for nutrition" and "formulation for consumption for pleasure" also include the ready-to-use products and foodstuffs (ready-to-consume or as semi-finished foodstuff goods) defined above. It goes without saying that the designations used in the context of the present text for certain groups of articles and certain formulations in some cases include products which can fall under several designations. Thus, for example, there are formulations for nutrition which at the same time serve for consumption for pleasure, which can be, in particular, foodstuffs. All the designations have the common feature, however, that they relate to articles (products) which are to be introduced into the human oral cavity in order to cause a smell or flavour impression there.

In odoriferous and/or aroma substance compositions according to the invention which comprise (a) 4-methyl-delta-hexylactone and (b) one, several or all of the compounds chosen from the group consisting of (i) menthol, (ii) (−)-carvone, (iii) menthone, (iv) isomenthone, the 4-methyl-delta-hexylactone to be employed according to the invention is already capable in low dosages of rounding off the overall profile of the smell or flavour of the odoriferous or aroma substance composition, and in particular of imparting more authenticity and naturalness to the composition.

In the case of a reconstituted (recombined, reconstructed), i.e. non-natural peppermint oil (which contains significant amounts of menthol) or spearmint oil (which contains significant amounts of (−)-carvone), the naturalness and authenticity are in each case increased significantly by the addition of 4-methyl-delta-hexylactone of the formula A, in particular in the abovementioned amounts, in particular because of the hay and coumarin notes imparted by the 4-methyl-delta-hexylactone, which are likewise present in natural peppermint oil and spearmint oil.

By incorporation of the compound (c) nonenolide (2-nonen-4-olide; 4-hydroxy-2-nonenoic acid lactone; IUPAC name: 5-pentyl-5H-furan-2-one, 5-pentyl-2(5H)-furanone) of the formula C:

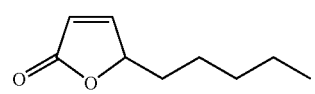

C into a perfumed or aromatized article according to the invention, in particular an odoriferous or aroma substance composition according to the invention, the hay and coumarin notes imparted, modified and/or intensified by the 4-methyl-delta-hexylactone of the formula A to be employed according to the invention in particular have a more intense effect, so that an even greater naturalness and authenticity can be achieved in respect of these notes, in particular in the preparation of reconstituted (recombined, reconstructed), i.e. non-natural peppermint and/or spearmint oils or aromas.

In this context, the nonenolide of the formula C can be in the form of the (R) configuration or (S) configuration or any desired mixture of the enantiomers, in particular in the form of the racemate.

In this context, it is to be mentioned that nonenolide of the formula C has the effect of a more intense coumarinic and a less pronounced hay-like note in the combination with 4-methyl-delta-hexylactone of the formula A. The combination of the compounds of the formulae A and C thereby renders possible tailoring of the hay and coumarin notes, so that a very balanced sensory profile of these two notes can also be achieved.

Nonenolide of the formula C is known and can be prepared, for example, in accordance with J. Food Science 1978, 43, 1248-1252 (racemic synthesis) or J. Org. Chem. 1995, 60, 5628-5633 (enantioselective synthesis).

In U.S. Pat. No. 3,767,427 it is stated that 4-hydroxy-2-nonenoic acid lactone (nonenolide of the formula C) per se has a strong smell of sweet coconut and deep-fried food. U.S. Pat. No. 3,767,427 describes (substantially fat-free) food-stuffs containing an amount of nonenolide in the range of 0.1-20 ppm, as a result of which a fatty, deep-fried food smell and flavour note is imparted to the foodstuff, in particular in combination with unsaturated delta-lactones having 7 to 12 carbon atoms or 2,4-decadienal. In this manner, a fatty, deep-fried food smell and flavour impression can be imparted to products such as baked potato crisps or margarine.

According to J. Food Science 1978, 43, 1248-1252, 2.5 ppm of nonenolide was added to cottonseed oil and the mixture was evaluated organoleptically by a panel, nutty, deep-fried food notes being found, some panellists also mentioning butter-like notes.

Agr. Biol. Chem. 1970, 34, 1745-1747 describes unsaturated gamma-lactones (as nonenolide is) on the whole as fatty, grass-like and sweetish.

J. Agric. Food Chem. 1997, 45, 1329-1332 reports on the results of aroma extract dilution analysis of boiled huitlacoche mushrooms. 2-Nonenoic acid gamma-lactone (nonenolide of the formula C) was identified by means of GC/olfactometry and was described in terms of smell as "coconut".

In Biosci. Biotech. Biochem. 1993, 57, 79-81, a fraction of various lactones was obtained from a volatile condensate from semi-fermented pouchong tea. The authors presume that this lactone fraction, which contained, inter alia, nonenolide as a trace component, contributes towards the characteristic smell of pouchong tea.

According to J. Agric. Food Chem. 1993, 41, 2385-2390, oxidative decomposition of (E,E)-2,4-decadienal in an aqueous medium at a pH of 6.5 gave a product mixture which contained, inter alia, 1.5% nonenolide.

The saturated gamma-nonalactone, which is structurally quite similar to the nonenolide of the formula C to be employed according to the invention, is known as a substance which smells and tastes of coconut (cf. K. Bauer et al., Common Fragrance and Flavor Materials, 4th edition, Wiley-VCH, Weinheim 2001 or also Tobacco Science 1976, 20, 125-133).

Some of the extracts or fractions in each case investigated in the documents Planta Medica 1985, 533-534 and Tobacco Science 1976, 20, 125-133 already mentioned above contained both the saturated gamma-nonalactone and 4-methyl-delta-hexylactone of the formula A, but not the compound of the formula C which is preferably to be employed according to the invention.

Summarizing, the following odoriferous or aroma substance compositions (mixtures) according to the invention therefore have a surprising smell and/or flavour quality:

odoriferous or aroma substance mixtures (=compositions) comprising 4-methyl-delta-hexylactone and one or more further odoriferous or aroma substances, one, several or all of the smell or flavour impressions of hay, coumarin, lactone and/or richness in the mouth being imparted to, modified in and/or intensified in the composition by the 4-methyl-delta-hexylactone;

odoriferous or aroma substance mixtures (=compositions) comprising 4-methyl-delta-hexylactone and one, several or all of the compounds of group (b) (i) menthol and/or (ii) (−)-carvone and/or (iii) menthone and/or (iv) isomenthone and one or more further odoriferous or aroma substances.

It is furthermore to be stated that in particular odoriferous or aroma substance compositions and corresponding articles comprising (a) 4-methyl-delta-hexylactone,
(b) (i) l-menthol and/or (ii) (−)-carvone
and optionally
(c) nonenolide are very particularly preferred, since such combinations represent an outstanding basis for the preparation of reconstituted (i.e. non-natural) peppermint and spearmint aromas and peppermint oils and spearmint oils.

The use according to the invention of 4-methyl-delta-hexylactone corresponds to a method according to the invention for imparting, modifying and/or intensifying one or more smell or flavour impressions from the group consisting of hay, coumarin, lactone and richness in the mouth, 4-methyl-delta-hexylactone or an odoriferous or aroma substance composition according to the invention comprising 4-methyl-delta-hexylactone (preferably in one of the embodiments described above as preferred) being brought into contact or mixed with a product.

The sensory properties, material properties (such as solubility in the usual solvents) and the compatibility with the usual further constituents of odoriferous or aroma substance compositions underline the particular suitability of 4-methyl-delta-hexylactone for the intended uses mentioned.

The invention also relates to a process for the preparation of an odoriferous or aroma substance composition, with the following step: Mixing of 4-methyl-delta-hexylactone with conventional constituents of an odoriferous or aroma substance composition, the 4-methyl-delta-hexylactone being employed in an amount which is sufficient to impart, to modify and/or to intensify one or more smell or flavour impressions from the group consisting of hay, coumarin, lactone and richness in the mouth in the odoriferous or aroma substance composition. Preferably, in this context the said odoriferous or aroma substance composition is an odoriferous or aroma substance composition according to the invention. In this case, (a) 4-methyl-delta-hexylactone is mixed with (b) one, several or all of the compounds chosen from the group consisting of (i) menthol, (ii) (−)-carvone, (iii) menthone and (iv) isomenthone, and, preferably, (c) nonenolide and/or (d) menthyl acetate and optionally further (conventional) constituents of an odoriferous or aroma substance composition.

Ingredients with which 4-methyl-delta-hexylactone of the formula A (in one of the forms mentioned) can be combined are, for example:

preservatives, abrasives, antiacne agents, agents against ageing of the skin, antibacterial agents, anticellulitis agents, antidandruff agents, antiinflammatory agents, irritation-preventing agents, irritation-inhibiting agents, antimicrobial agents, antioxidants, astringents, perspiration-inhibiting agents, antiseptic agents, antistatics, binders, buffers, carrier materials, chelating agents, cell stimulants, cleansing agents, care agents, depilatory agents, surface-active substances, deodorizing agents, antiperspirants, softeners, emulsifiers, enzymes, essential oils, fibres, film-forming agents, fixatives, foam-forming agents, foam stabilizers, substances for preventing foaming, foam boosters, fungicides, gelling agents, gel-forming agents, hair care agents, hair shaping agents, hair straightening agents, moisture-donating agents, moisturizing substances, moisture-retaining substances, bleaching agents, strengthening agents, stain-removing agents, optically brightening agents, impregnating agents, dirt-repellent agents, friction-reducing agents, lubricants, moisturizing creams, ointments, opacifying agents, plasticizing agents, covering agents, polish, gloss agents, polymers, powders, proteins, re-oiling agents, abrading agents, silicones, skin soothing agents, skin cleansing agents, skin care agents, skin healing agents, skin lightening agents, skin protecting agents, skin softening agents, cooling agents, skin cooling agents, warming agents, skin warming agents, stabilizers, UV-absorbing agents, UV filters, detergents, fabric softeners, suspending agents, skin tanning agents, thickening agents, vitamins, oils, waxes, fats, phospholipids, saturated fatty acids, mono- or polyunsaturated fatty acids, alpha-hydroxy acids, polyhydroxy-fatty acids, liquefiers, dyestuffs, colour-protecting agents, pigments, anticorrosives, aromas, flavouring substances, odoriferous substances, polyols, surfactants, electrolytes, organic solvents or silicone derivatives.

Individual cooling active compounds which are preferred for use in the context of the present invention for incorporation into odoriferous or aroma substance compositions and articles according to the invention are listed below. The person skilled in the art can supplement the following list with a large number of further cooling active compounds; the cooling active compounds listed can also be employed in combination with one another: menthone glycerol acetal (trade name: Frescolat®MGA), menthyl lactate (trade name: Frescolat®ML, menthyl lactate is preferably l-menthyl lactate, in particular l-menthyl l-lactate substituted menthyl-3-carboxylic acid amides (e.g. menthyl-3-carboxylic acid N-ethylamide, also known as WS-3), 2-isopropyl-N-2,3-trimethylbutanamide (also known as WS-23), substituted cyclohexanecarboxylic acid amides, 3-menthoxypropane-1,2-diol, 2-hydroxyethyl menthyl carbonate, 2-hydroxypropyl menthyl carbonate, N-acetylglycine menthyl ester, isopulegol, menthyl hydroxycarboxylic acid esters (e.g. menthyl 3-hydroxybutyrate), monomenthyl succinate, 2-mercaptocyclodecanone, menthyl 2-pyrrolidin-5-onecarboxylate, 2,3-dihydroxy-p-menthane, 3,3,5-trimethylcyclohexanone glycerol ketal, 3-menthyl 3,6-di- and trioxaalkanoates, 3-menthyl methoxyacetate, icilin.

Particularly preferred cooling active compounds are: menthone glycerol acetal (trade name: Frescolat®MGA), menthyl lactate (preferably l-menthyl lactate, in particular l-menthyl l-lactate, trade name: Frescolat®ML), substituted menthyl-3-carboxylic acid amides (e.g. menthyl-3-carboxylic acid N-ethylamide), 2-isopropyl-N-2,3-trimethylbutanamide, 3-menthoxypropane-1,2-diol, 2-hydroxyethyl menthyl carbonate, 2-hydroxypropyl menthyl carbonate, isopulegol and monomenthyl succinate.

As already stated above, it is advantageous to employ some or several conventional odoriferous or aroma substances in odoriferous or aroma substance compositions according to the invention. Particularly interesting and natural novel and original smell or flavour notes can be created in this manner. Odoriferous or aroma substances which are advantageously suitable for combination are to be found e.g. in S. Arctander, Perfume and Flavor Materials, vol. I und II, Montclair, N.J. 1969, author and publisher, or K. Bauer et al., Common Fragrance and Flavor Materials, 4th edition, Wiley-VCH, Weinheim 2001. There may be mentioned specifically:
extracts from natural raw materials, such as essential oils, concretes, absolutes, resins, resinoids, balsams, tinctures, such as e.g.
amber tincture; amyris oil; angelica seed oil; angelica root oil; aniseed oil; valerian oil; basil oil; tree moss absolute; bay oil; *artemisia* oil; benzoin resin; bergamot oil; beeswax absolute; birch tar oil; bitter almond oil; bean leaf oil; buchu leaf oil; cabreuva oil; cade oil; calamus oil; camphor oil; cananga oil; cardamom oil; cascarilla oil; *cassia* oil; *cassia* absolute; castoreum absolute; cedar leaf oil; cedar wood oil; cistus oil; citronella oil; lemon oil; copaiva balsam; copaiva balsam oil; coriander oil; *costus* root oil; cumin oil; cypress oil; davana oil; dill weed oil; dill seed oil; eau de brouts absolute; oak moss absolute; elemi oil; tarragon oil; Eucalyptus citriodora oil; eucalyptus oil; fennel oil; spruce needle oil; galbanum oil; galbanum resin; geranium oil; grapefruit oil; guaiac wood oil; gurjunene balsam; gurjunene balsam oil; *helichrysum* absolute; *helichrysum* oil; ginger oil; iris root absolute; iris root oil; jasmine absolute; calamus oil; camomile oil blue; camomile oil Roman; carrot seed oil; cascarilla oil; pine needle oil; spearmint oil; caraway oil; labdanum oil; labdanum absolute; labdanum resin; lavandin absolute; lavandin oil; lavender absolute; lavender oil; lemon grass oil; lovage oil; lime oil distilled; lime oil pressed; linaloa oil; Litsea cubeba oil; bay leaf oil; mace oil; marjoram oil; mandarin oil; massoi bark oil; mimosa absolute; musk seed oil; musk tincture; muscatel sage oil; nutmeg oil; myrrh absolute; myrrh oil; myrtle oil; clove leaf oil; clove blossom oil; neroli oil; olibanum absolute; olibanum oil; opopanax oil; orange blossom absolute; orange oil; oregano oil; palmarosa oil; patchouli oil; *perilla* oil; Peru balsam oil; parsley leaf oil; parsley seed oil; petitgrain oil; peppermint oil; pepper oil; pimento oil; pine oil; poley oil; rose absolute; rose wood oil; rose oil; rosemary oil; sage oil Dalmatian; sage oil Spanish; sandalwood oil; celery seed oil; spike lavender oil; star aniseed oil; *styrax* oil; tagetes oil; fir needle oil; tea tree oil; turpentine oil; thyme oil; tolu balsam; tonka absolute; tuberose absolute; vanilla extract; violet leaf absolute; verbena oil; vetiver oil; juniper berry oil; wine yeast oil; wormwood oil; wintergreen oil; ylang oil; hyssop oil; civet absolute; cinnamon leaf oil; cinnamon bark oil and fractions thereof or constituents isolated therefrom; individual odoriferous substances from the group consisting of the hydrocarbons, such as e.g. 3-carene; α-pinene; β-pinene; α-terpinene; γ-terpinene; p-cymene; bisabolene; camphene; caryophyllene; cedrene; farnesene; limonene; longifolene; myrcene; ocimene; valencene; (E,Z)-1,3,5-undecatriene; styrene; diphenylmethane;

the aliphatic alcohols, such as e.g. hexanol; octanol; 3-octanol; 2,6-dimethylheptanol; 2-methyl-2-heptanol; 2-methyl-2-octanol; (E)-2-hexenol; (E) and (Z)-3-hexenol; 1-octen-3-ol; mixture of 3,4,5,6,6-pentamethyl-3/4-hepten-2-ol and 3,5,6,6-tetramethyl-4-methyleneheptan-2-ol; (E,Z)-2,6-nonadienol; 3,7-dimethyl-7-methoxyoctan-2-ol; 9-decenol; 10-undecenol; 4-methyl-3-decen-5-ol;

the aliphatic aldehydes and acetals thereof, such as e.g. hexanal; heptanal; octanal; nonanal; decanal; undecanal; dodecanal; tridecanal; 2-methyloctanal; 2-methylnonanal; (E)-2-hexenal; (Z)-4-heptenal; 2,6-dimethyl-5-heptenal; 10-undecenal; (E)-4-decenal; 2-dodecenal; 2,6,10-trimethyl-9-undecenal; 2,6,10-trimethyl-5,9-undecadienal; heptanal diethyl acetal; 1,1-dimethoxy-2,2,5-trimethyl-4-hexene; citronellyloxyacetaldehyde; 1-(1-methoxy-propoxy)-(E/Z)-3-hexene;

the aliphatic ketones and oximes thereof, such as e.g. 2-heptanone; 2-octanone; 3-octanone; 2-nonanone; 5-methyl-3-heptanone; 5-methyl-3-heptanone oxime; 2,4,4,7-tetramethyl-6-octen-3-one; 6-methyl-5-hepten-2-one;

the aliphatic sulfur-containing compounds, such as e.g. 3-methylthio-hexanol; 3-methylthiohexyl acetate; 3-mercaptohexanol; 3-mercaptohexyl acetate; 3-mercaptohexyl butyrate; 3-acetylthiohexyl acetate; 1-menthene-8-thiol;

the aliphatic nitriles, such as e.g. 2-nonenoic acid nitrile; 2-undecenoic acid nitrile; 2-tridecenoic acid nitrile; 3,12-tridecadienoic acid nitrile; 3,7-dimethyl-2,6-octadienoic acid nitrile; 3,7-dimethyl-6-octenoic acid nitrile;

the esters of aliphatic carboxylic acids, such as e.g. (E)- and (Z)-3-hexenyl formate; ethyl acetoacetate; isoamyl acetate; hexyl acetate; 3,5,5-trimethylhexyl acetate; 3-methyl-2-butenyl acetate; (E)-2-hexenyl acetate; (E)- and (Z)-3-hexenyl acetate; octyl acetate; 3-octyl acetate; 1-octen-3-yl acetate; ethyl butyrate; butyl butyrate; isoamyl butyrate; hexyl butyrate; (E)- and (Z)-3-hexenyl isobutyrate; hexyl crotonate; ethyl isovalerate; ethyl 2-methylpentanoate; ethyl hexanoate; allyl hexanoate; ethyl heptanoate; allyl heptanoate; ethyl octanoate; ethyl (E,Z)-2,4-decadienoate; methyl 2-octynate;

methyl 2-nonynate; allyl 2-isoamyloxyacetate; methyl 3,7-dimethyl-2,6-octadienoate; 4-methyl-2-pentyl-crotonate;

the acyclic terpene alcohols, such as e.g. citronellol; geraniol; nerol; linalool; lavadulol; nerolidol; farnesol; tetrahydrolinalool; tetrahydrogeraniol; 2,6-dimethyl-7-octen-2-ol; 2,6-dimethyloctan-2-ol; 2-methyl-6-methylen-7-octen-2-ol; 2,6-dimethyl-5,7-octadien-2-ol; 2,6-dimethyl-3,5-octadien-2-ol; 3,7-dimethyl-4,6-octadien-3-ol; 3,7-dimethyl-1,5,7-octatrien-3-ol; 2,6-dimethyl-2,5,7-octatrien-1-ol; and formates, acetates, propionates, isobutyrates, butyrates, isovalerates, pentanoates, hexanoates, crotonates, tiglinates and 3-methyl-2-butenoates thereof;

the acyclic terpene aldehydes and ketones, such as e.g. geranial; neral; citronellal; 7-hydroxy-3,7-dimethyloctanal; 7-methoxy-3,7-dimethyloctanal; 2,6,10-trimethyl-9-undecenal; geranylacetone; and the dimethyl and diethyl acetals of geranial, neral, 7-hydroxy-3,7-dimethyloctanal;

the cyclic terpene alcohols, such as e.g. isopulegol; alpha-terpineol; terpinen-4-ol; menthan-8-ol; menthan-1-ol; menthan-7-ol; borneol; isoborneol; linalool oxide; nopol; cedrol; ambrinol; vetiverol; guaiol; and formates, acetates, propionates, isobutyrates, butyrates, isovalerates, pentanoates, hexanoates, crotonates, tiglinates and 3-methyl-2-butenoates thereof;

the cyclic terpene aldehydes and ketones, such as e.g. 8-mercaptomenthan-3-one; camphor; fenchone; alpha-ionone; beta-ionone; alpha-n-methylionone; beta-n-methylionone; alpha-isomethylionone; beta-isomethylionone; alpha-irone; alpha-damascone; beta-damascone; beta-damascenone; delta-damascone; gamma-damascone; 1-(2,4,4-trimethyl-2-cyclohexen-1-yl)-2-buten-1-one; 1,3,4,6,7,8a-hexahydro-1,1,5,5-tetramethyl-2H-2,4-a-methanonaphthalen-8(5H)-one; 2-methyl-4-(2,6,6-trimethyl-1-cyclohexen-1-yl-2-butenal; nootkatone; dihydronootkatone; 4,6,8-megastigmatrien-3-one; alpha-sinensal; beta-sinensal; acetylated cedar wood oil (methyl cedryl ketone);

the cyclic alcohols, such as e.g. 4-tert-butylcyclohexanol; 3,3,5-trimethylcyclo-hexanol; 3-isocamphylcyclohexanol; 2,6,9-trimethyl-Z2,Z5,E9-cyclododecatrien-1-ol; 2-isobutyl-4-methyltetrahydro-2H-pyran-4-ol;

the cycloaliphatic alcohols, such as e.g. alpha, 3,3-trimethyl-cyclohexylmethanol; 1-(4-isopropylcyclohexyl)ethanol; 2-methyl-4-(2,2,3-trimethyl-3-cyclopent-1-yl)butanol; 2-methyl-4-(2,2,3-trimethyl-3-cyclopent-1-yl)-2-buten-1-ol; 2-ethyl-4-(2,2,3-trimethyl-3-cyclopent-1-yl)-2-buten-1-ol; 3-methyl-5-(2,2,3-trimethyl-3-cyclopent-1-yl)-pentan-2-ol; 3-methyl-5-(2,2,3-trimethyl-3-cyclopent-1-yl)-4-penten-2-ol; 3,3-dimethyl-5-(2,2,3-trimethyl-3-cyclopent-1-yl)-4-penten-2-ol; 1-(2,2,6-trimethylcyclohexyl)pentan-3-ol; 1-(2,2,6-trimethylcyclohexyl)hexan-3-ol;

the cyclic and cycloaliphatic ethers, such as e.g. 1,8-cineol (eucalyptol); cedryl methyl ether; cyclododecyl methyl ether; 1,1-dimethoxycyclododecane; (ethoxymethoxy)cyclododecane; alpha-cedrene epoxide; 3a,6,6,9a-tetramethyl-dodecahydronaphtho[2,1-b]furan; 3a-ethyl-6,6,9a-trimethyldode-cahydronaphtho[2,1-b]furan; 1,5,9-trimethyl-13-oxabicyclo[10.1.0]trideca-4,8-diene; rose oxide; 2-(2,4-dimethyl-3-cyclohexen-1-yl)-5-methyl-5-(1-methylpropyl)-1,3-dioxane;

the cyclic and macrocyclic ketones, such as e.g. 4-tert-butyl-cyclohexanone; 2,2,5-trimethyl-5-pentylcyclopentanone; 2-heptylcyclopentanone; 2-pentylcyclopentanone; 2-hydroxy-3-methyl-2-cyclopenten-1-one; 3-methyl-cis-2-penten-1-yl-2-cyclopenten-1-one; 3-methyl-2-pentyl-2-cyclopenten-1-one; 3-methyl-4-cyclopentadecenone; 3-methyl-5-cyclopentadecenone; 3-methylcyclo-pentadecanone; 4-(1-ethoxyvinyl)-3,3,5,5-tetramethylcyclohex-anone; 4-tert-pentylcyclohexanone; 5-cyclohexadecen-1-one; 6,7-dihydro-1,1,2,3,3-pentamethyl-4(5H)-indanone; 8-cyclohexadecen-1-one; 9-cycloheptadecen-1-one; cyclopentadecanone; cyclohexadecanone;

the cycloaliphatic aldehydes, such as e.g. 2,4-dimethyl-3-cyclohexenecarbaldehyde; 2-methyl-4-(2,2,6-trimethyl-cyclohexen-1-yl)-2-butenal; 4-(4-hydroxy-4-methyl pentyl)-3-cyclohexenecarbaldehyde; 4-(4-methyl-3-penten-1-yl)-3-cyclohexenecarbaldehyde;

the cycloaliphatic ketones, such as e.g. 1-(3,3-dimethylcyclohexyl)-4-penten-1-one; 2,2-dimethyl-1-(2,4-dimethyl-3-cyclohexen-1-yl)-1-propanone; 1-(5,5-dimethyl-1-cyclohexen-1-yl)-4-penten-1-one; 2,3,8,8-tetramethyl-1,2,3,4,5,6,7,8-octahydro-2-naphthalenyl methyl ketone; methyl 2,6,10-trimethyl-2,5,9-cyclododecatrienyl ketone; tert-butyl (2,4-dimethyl-3-cyclohexen-1-yl) ketone;

the esters of cyclic alcohols, such as e.g. 2-tert-butylcyclohexyl acetate; 4-tert-butylcyclohexyl acetate; 2-tert-pentylcyclohexyl acetate; 4-tert-pentylcyclohexyl acetate; 3,3,5-trimethylcyclohexyl acetate; decahydro-2-naphthyl acetate; 2-cyclopentylcyclopentyl crotonate; 3-pentyltetrahydro-2H-pyran-4-yl acetate; decahydro-2,5,5,8a-tetramethyl-2-naphthyl acetate; 4,7-methano-3a,4,5,6,7,7a-hexahydro-5- and -6-indenyl acetate; 4,7-methano-3a,4,5,6,7,7a-hexahydro-5- and -6-indenyl propionate; 4,7-methano-3a,4,5,6,7,7a-hexahydro-5- and -6-indenyl isobutyrate; 4,7-methanooctahydro-5- and 6-indenyl acetate;

the esters of cycloaliphatic alcohols, such as e.g. 1-cyclohexylethyl crotonate;

the esters of cycloaliphatic carboxylic acids, such as e.g. allyl 3-cyclohexylpropionate; allyl cyclohexyloxyacetate; cis- and trans-methyl dihydrojasmonate; cis- and trans-methyl jasmonate; methyl 2-hexyl-3-oxocyclopentanecarboxylate; ethyl 2-ethyl-6,6-dimethyl-2-cyclohexenecarb-oxylate; ethyl 2,3,6,6-tetramethyl-2-cyclohexenecarboxylate; ethyl 2-methyl-1,3-dioxolane-2-acetate;

the araliphatic alcohols, such as e.g. benzyl alcohol; 1-phenylethyl alcohol; 2-phenylethyl alcohol; 3-phenylpropanol; 2-phenylpropanol; 2-phenoxyethanol; 2,2-dimethyl-3-phenylpropanol; 2,2-dimethyl-3-(3-methylphenyl)propanol; 1,1-dimethyl-2-phenylethyl alcohol; 1,1-dimethyl-3-phenylpropanol; 1-ethyl-1-methyl-3-phenylpropanol; 2-methyl-5-phenylpentanol; 3-methyl-5-phenylpentanol; 3-phenyl-2-propen-1-ol; 4-methoxybenzyl alcohol; 1-(4-isopropylphenyl)ethanol;

the esters of araliphatic alcohols and aliphatic carboxylic acids, such as e.g.: benzyl acetate; benzyl propionate; benzyl isobutyrate; benzyl isovalerate; 2-phenylethyl acetate; 2-phenylethyl propionate; 2-phenylethyl isobutyrate; 2-phenylethyl isovalerate; 1-phenylethyl acetate; alpha-trichloromethylbenzyl acetate; alpha,alpha-dimethylphenylethyl acetate; alpha,alpha-dimethylphenylethyl butyrate; cinnamyl acetate; 2-phenoxyethyl isobutyrate; 4-methoxybenzyl acetate;

the araliphatic ethers, such as e.g. 2-phenylethyl methyl ether; 2-phenylethyl isoamyl ether; 2-phenylethyl 1-ethoxyethyl ether; phenylacetaldehyde dimethyl acetal; phenylacetaldehyde diethyl acetal; hydratropaaldehyde dimethyl acetal; phenylacetaldehyde glycerol acetal; 2,4,6-trimethyl-4-phenyl-1,3-dioxane; 4,4a,5,9b-tetrahydroindeno[1,2-d]-m-dioxin; 4,4a,5,9b-tetrahydro-2,4-dimethylindeno[1,2-d]-m-dioxin;

the aromatic and araliphatic aldehydes, such as e.g. benzaldehyde; phenylacetaldehyde; 3-phenylpropanal; hydratropaaldehyde; 4-methylbenzaldehyde; 4-methylphenylacetaldehyde; 3-(4-ethylphenyl)-2,2-dimethylpropanal; 2-methyl-3-(4-isopropylphenyl)propanal; 2-methyl-3-(4-tertbutylphenyl)propanal; 2-methyl-3-(4-isobutylphenyl) propanal; 3-(4-tert-butylphenyl)propanal; cinnamaldehyde; alpha-butylcinnamaldehyde; alpha-amylcinnam-aldehyde; alpha-hexylcinnamaldehyde; 3-methyl-5-phenylpentanal; 4-methoxy-benzaldehyde; 4-hydroxy-3-methoxybenzaldehyde; 4-hydroxy-3-ethoxybenzaldehyde; 3,4-methylenedioxybenzaldehyde; 3,4-dimethoxybenzaldehyde; 2-methyl-3-(4-methoxyphenyl)propanal; 2-methyl-3-(4-methylenedioxyphenyl)propanal;

the aromatic and araliphatic ketones, such as e.g. acetophenone; 4-methyl-acetophenone; 4-methoxyacetophenone; 4-tert-butyl-2,6-dimethylacetophenone; 4-phenyl-2-butanone; 4-(4-hydroxyphenyl)-2-butanone; 1-(2-naphthalenyl)-ethanone; 2-benzofuranylethanone; (3-methyl-2-benzofuranyl)ethanone; benzo-phenone; 1,1,2,3,3,6-hexamethyl-5-indanyl methyl ketone; 6-tert-butyl-1,1-dimethyl-4-indanyl methyl ketone; 1-[2,3-dihydro-1,1,2,6-tetramethyl-3-(1-methyl-ethyl)-1H-5-indenyl]ethanone; 5',6',7',8'-tetrahydro-3',5',5',6',8',8'-hexamethyl-2-acetonaphthone;

the aromatic and araliphatic carboxylic acids and esters thereof, such as e.g. benzoic acid; phenylacetic acid; methyl benzoate; ethyl benzoate; hexyl benzoate; benzyl benzoate; methylphenyl acetate; ethylphenyl acetate; geranylphenyl acetate; phenylethyl-phenyl acetate; methyl cinnamate; ethyl cinnamate; benzyl cinnamate; phenylethyl cinnamate; cinnamyl cinnamate; allyl phenoxyacetate; methyl salicylate; isoamyl salicylate; hexyl salicylate; cyclohexyl salicylate; cis-3-hexenyl salicylate; benzyl salicylate; phenylethyl salicylate; methyl 2,4-dihydroxy-3,6-dimethylbenzoate; ethyl 3-phenylglycidate; ethyl 3-methyl-3-phenylglycidate;

the nitrogen-containing aromatic compounds, such as e.g. 2,4,6-trinitro-1,3-dimethyl-5-tert-butylbenzene; 3,5-dinitro-2,6-dimethyl-4-tert-butylacetophenone; cinnamic acid nitrile; 3-methyl-5-phenyl-2-pentenoic acid nitrile; 3-methyl-5-phenylpentanoic acid nitrile; methyl anthranilate; methyl N-methylanthranilate; Schiff's bases of methyl anthranilate with 7-hydroxy-3,7-dimethyloctanal, 2-methyl-3-(4-tert-butylphenyl)propanal or 2,4-dimethyl-3-cyclohexenecarbaldehyde; 6-isopropylquinoline; 6-isobutylquinoline; 6-sec-butylquinoline; 2-(3-phenylpropyl)pyridine; indole; skatole; 2-methoxy-3-isopropylpyrazine; 2-isobutyl-3-methoxypyrazine;

the phenols, phenyl ethers and phenyl esters, such as e.g. estragole; anethole; eugenol; eugenyl methyl ether; isoeugenol; isoeugenyl methyl ether; thymol; carvacrol; diphenyl ether; beta-naphthyl methyl ether; beta-naphthyl ethyl ether; beta-naphthyl isobutyl ether; 1,4-dimethoxybenzene; eugenyl acetate; 2-methoxy-4-methylphenol; 2-ethoxy-5-(1-propenyl)phenol; p-cresyl phenylacetate;

the heterocyclic compounds, such as e.g. 2,5-dimethyl-4-hydroxy-2H-furan-3-one; 2-ethyl-4-hydroxy-5-methyl-2H-furan-3-one; 3-hydroxy-2-methyl-4H-pyran-4-one; 2-ethyl-3-hydroxy-4H-pyran-4-one;

the lactones, such as e.g. 1,4-octanolide; 3-methyl-1,4-octanolide; 1,4-nonanolide; 1,4-decanolide; 8-decen-1,4-olide; 1,4-undecanolide; 1,4-dodecanolide; 1,5-decanolide; 1,5-dodecanolide; 4-methyl-1,4-decanolide; 1,15-pentadecanolide; cis- and trans-11-pentadecen-1,15-olide; cis- and trans-12-pentadecen-1,15-olide; 1,16-hexadecanolide; 9-hexadecen-1,16-olide; 10-oxa-1,16-hexadecanolide; 11-oxa-1,16-hexadecanolide; 12-oxa-1,16-hexadecanolide; ethylene 1,12-dodecanedioate; ethylene 1,13-tridecanedioate; coumarin; 2,3-dihy-drocoumarin; octahydrocoumarin.

Odoriferous or aroma substance compositions according to the invention which comprise 4-methyl-delta-hexylactone can be in liquid form, undiluted or diluted with a solvent and employed as such for perfuming or aromatizing. Suitable solvents for this are e.g. ethanol, isopropanol, diethylene glycol monoethyl ether, glycerol, propylene glycol, 1,2-butylene glycol, dipropylene glycol, diethyl phthalate, triethyl citrate, isopropyl myristate, triacetin etc.

Odoriferous or aroma substance compositions according to the invention which comprise 4-methyl-delta-hexylactone can furthermore be adsorbed on a carrier substance, which ensures both a fine distribution of the odoriferous or aroma substances in the product and a controlled release during use. Such carriers can be porous inorganic materials, such as light sulfate, silica gels, zeolites, gypsums, clays, clay granules, gas concrete etc., or organic materials, such as woods, cellulose-based substances, sugars, dextrins (e.g. maltodextrin) or plastics, such as PVC, polyvinyl acetates or polyurethanes. The combination of composition according to the invention and carrier substance is an example of an article according to the invention.

Odoriferous or aroma substance compositions according to the invention which comprise 4-methyl-delta-hexylactone can also be in a microencapsulated or spray-dried form or in the form of inclusion complexes or extrusion products (i.e. articles according to the invention) and can be added in this form e.g. to a product to be perfumed or aromatized.

The properties of compositions modified in this manner can optionally be optimized further in respect of a more controlled release of fragrance by so-called "coating" with suitable materials, for which purpose waxy plastics, e.g. polyvinyl alcohol, are preferably used. The resulting products in turn are articles according to the invention.

The microencapsulation of the odoriferous or aroma substance compositions according to the invention to give articles according to the invention can be carried out, for example, by the so-called coacervation process (seamless capsule, based on gelatine and/or alginate) with the aid of capsule materials e.g. of polyurethane-like substances or soft gelatine. The spray-dried odoriferous or aroma substance compositions can be prepared, for example, by spray drying of an emulsion or dispersion containing the odoriferous or aroma substance composition, it being possible to use modified starches, proteins, dextrin and plant gums as carrier substances. Inclusion complexes can be prepared e.g. by introducing dispersions of the odoriferous or aroma substance composition and cyclodextrins or urea derivatives into a suitable solvent, e.g. water. Extrusion products can be obtained by melting the odoriferous or aroma substance compositions with a suitable waxy substance and by extrusion with subsequent solidification, optionally in a suitable solvent, e.g. isopropanol.

Odoriferous substance compositions which comprise 4-methyl-delta-hexylactone can be used in concentrated form, in solutions or in the modified form described above for the preparation of perfumed articles according to the invention, such as e.g. perfume extracts, perfume waters, toilet waters, shaving lotions, cologne waters, pre-shave products, splash colognes and perfumed freshening wipes, as well as perfuming of acid, alkaline and neutral cleaning compositions, such as e.g. floor cleaners, window glass cleaners, dishwashing compositions, bath and sanitary cleaners, scouring milk, solid and liquid WC cleaners, powdered and foamed carpet cleaners, textile fresheners, ironing aids, liquid detergents, pulverulent detergents, laundry pretreatment compositions, such as bleaching compositions, soaking compositions and stain removers, laundry softeners, washing soaps, washing tablets, disinfectants, surface disinfectants and air fresheners in liquid or gelatinous form or in a form applied to a solid carrier, aerosol sprays, waxes and polishes, such as furniture polishes, floor waxes, shoe creams as well as body care compositions, such as e.g. solid and liquid soaps, shower gels, shampoos, shaving soaps, shaving foams, bath oils, cosmetic emulsions of the oil-in-water, of the water-in-oil and of the water-in-oil-in-water type, such as e.g. skin creams and lotions, face creams and lotions, sunscreen creams and lotions, after-sun creams and lotions, hand creams and lotions, foot creams and lotions, depilatory creams and lotions, after-shave creams and lotions, tanning creams and lotions, hair care products, such as e.g. hair sprays, hair gels, hair setting lotions, hair conditioners, permanent and semi-permanent hair colouring compositions, hair shaping compositions, such as cold waving compositions and hair straightening compositions, hair waters, hair creams and lotions, deodorants and antiperspirants, such as e.g. underarm sprays, roll-ons, deodorant sticks, deodorant creams, products for decorative cosmetics, such as e.g. eye shadows, nail varnishes, make-up, lipsticks, mascara as well as candles, lamp oils, joss sticks, insecticides, repellents and fuels.

The 4-methyl-delta-hexylactone to be employed according to the invention can be incorporated into aromatized articles or articles to be aromatized, in particular into formulations for nutrition, oral care or consumption for pleasure.

Formulations for nutrition or consumption for pleasure are e.g. baked goods (e.g. bread, dry biscuits, cakes, other baked products), confectionery (e.g. chocolate, chocolate bar products, other bar products, fruit gum, hard and soft caramels, chewing gum), alcoholic or non-alcoholic drinks (e.g. coffee, tea, wine, wine-containing drinks, beer, beer-containing drinks, liqueurs, schnapps, brandies, (fruit-containing) carbonated drinks, isotonic drinks, refreshing drinks, nectars, fruit and vegetable juices, fruit or vegetable juice formulations), instant drinks (e.g. instant cocoa drinks, instant tea drinks, instant coffee drinks), meat products (e.g. ham, fresh sausage or uncooked sausage formulations, seasoned or marinated fresh or salted meat products), eggs or egg products (dried egg, egg white, egg yolk), cereal products (e.g. breakfast cereals, muesli bars, precooked ready-made rice products), dairy products (e.g. milk drinks, milk ice, yoghurt, kefir, fresh cheese, soft cheese, hard cheese, dried milk powder, whey, butter, buttermilk, products containing partly or completely hydrolysed milk protein), products from soya protein or other soya bean fractions (e.g. soya milk and products produced therefrom, soya lecithin-containing formulations, fermented products, such as tofu or tempe or products produced therefrom, soya sauces), fruit formulations (e.g. preserves, fruit-flavoured ice-cream, fruit sauces, fruit fillings), vegetable formulations (e.g. ketchup, sauces, dried vegetables, frozen vegetables, precooked vegetables, vegetables marinated in vinegar, cooked vegetables), nibbles (e.g. baked or fried potato crisps or potato paste products, bread paste products, extrudates based on maize or peanuts), fat- and oil-based products or emulsions thereof (e.g. mayonnaise, remoulade, dressings, spice formulations), other ready-made dishes and soups (e.g. dried soups, instant soups, precooked soups), spices, spice mixtures and, in particular, sprinkling spices (seasonings), which are used, for example, in the snacks sector. After incorporation of the compound according to the invention, these formulations are formulations according to the invention (as an example of articles according to the invention).

Formulations according to the invention can be e.g. in the form of semi-finished goods or in the form of a spice mixture.

Formulations according to the invention can serve in particular as semi-finished goods for the preparation of further formulations for nutrition or consumption for pleasure, in particular in spray-dried form. Formulations according to the invention can also be in the form of capsules, tablets (non-coated and coated tablets, e.g. coatings which are resistant to gastric juice), dragées, granules, pellets, solid mixtures, dispersions in liquid phases, in the form of emulsions, in the form of powders, in the form of solutions, in the form of pastes or in the form of other formulations which can be swallowed or chewed in the form of food supplements.

Preferred products which are suitable for consumption are, for example, baked goods (biscuits, cakes, muffins, waffles, baking mixtures), confectionery (hard caramels, soft caramels, bonbons for chewing, compressed tablets, dragées, sugar beads, sugar fillings), dairy products (yoghurts, puddings, ice-cream), chocolate goods (white, light or dark chocolate, chocolate bars), creamy compositions (fillings for baked goods, such as e.g. biscuit fillings, creamy fillings for chocolates, creamy fillings for bars), chewing gums (sugar-free, sugar-containing, strips, compressed tablets, dragées), snacks and snack mixtures, water-soluble powder products and mixtures for sprinkling on (toppings), compare also the above statements regarding preferred (ready-to-use) formulations according to the invention.

Further conventional active compounds, base substances, auxiliary substances and additives for formulations according to the invention for nutrition, oral care or consumption for pleasure can be present in amounts of from 5 to 99.9 wt. %, preferably 10 to 80 wt. %, based on the total weight of the formulation. The formulations can furthermore contain water in an amount of up to 99.9 wt. %, preferably 5 to 80 wt. %, based on the total weight of the formulation.

According to a preferred embodiment, the formulations according to the invention (as examples of articles according to the invention) comprising an odoriferous or aroma substance mixture according to the invention are prepared by incorporating the 4-methyl-delta-hexylactone, in substance, as a solution (e.g. in ethanol, water or 1,2-propylene glycol) or in the form of a mixture with a solid or liquid carrier substance (e.g. maltodextrin, starch, silica gel), other aromas or aroma substances and optionally further auxiliaries and/or stabilizers (e.g. natural or synthetic polysaccharides and/or plant gums, such as modified starches or gum arabic) into a base formulation for nutrition, oral care or consumption for pleasure. Advantageously, formulations according to the invention in the form of a solution and/or suspension or emulsion can also be converted into a solid formulation (semi-finished goods) according to the invention by spray drying. In this context, other aromas or aroma substances which are employed are in particular—as stated above—one, several or all of the compounds chosen from the group consisting of (i) menthol, (ii) (−)-carvone, (iii) menthone and (iv) isomenthone and, preferably, (c) nonenolide and/or (d) menthyl acetate.

The spray-dried solid formulations according to the invention (as an example of articles according to the invention) are particularly suitable as semi-finished goods for the preparation of further formulations according to the invention. The spray-dried solid formulations according to the invention preferably comprise 50 to 95% wt. % of carrier substances, in particular maltodextrin and/or starch, 5 to 40% of auxiliary substances, preferably natural or synthetic polysaccharides and/or plant gums, such as modified starches or gum arabic.

According to a further preferred embodiment, for the preparation of formulations according to the invention the 4-methyl-delta-hexylactone to be employed according to the invention or an odoriferous or aroma substance composition according to the invention and optionally other constituents of the formulation according to the invention are first incorporated into emulsions, into liposomes, e.g. starting from phosphatidylcholine, into microspheres, into nanospheres or also into capsules, granules or extrudates of a matrix which is suitable e.g. for foodstuffs and compositions for consumption for pleasure, e.g. of starch, starch derivatives (e.g. modified starch), cellulose or cellulose derivatives (e.g. hydroxypropylcellulose), other polysaccharides (e.g. dextrin, alginate, curdlan, carrageenan, chitin, chitosan, pullulan), natural fats, natural waxes (e.g. beeswax, carnauba wax), of proteins, e.g. gelatine, or other natural products (e.g. shellac). In this context, depending on the matrix, the products can be obtained by spray drying, spray granulation, melt granulation, coacervation, coagulation, extrusion, melt extrusion, emulsion processes, coating or other suitable encapsulation processes and optionally a suitable combination of the abovementioned processes. In a further preferred preparation process for a formulation according to the invention, the 4-methyl-delta-hexylactone or an odoriferous or aroma substance composition according to the invention comprising 4-methyl-delta-hexylactone is first complexed with one or more suitable complexing agents, for example with cyclodextrins or cyclodextrin derivatives, preferably α- or β-cyclodextrin, and are employed in this complexed form.

A formulation according to the invention in which the matrix is chosen such that 4-methyl-delta-hexylactone or an odoriferous or aroma substance composition according to the invention is released from the matrix in delayed form, so that a long-lasting action is obtained, is particularly preferred. A fat, wax, polysaccharide or protein matrix is particularly preferred in this respect.

Further constituents of formulations according to the invention for nutrition or consumption for pleasure which can be used are conventional base substances, auxiliary substances and additives for foodstuffs or compositions for consumption for pleasure, e.g. water, mixtures of fresh or processed, plant or animal base substances or raw materials (e.g. raw, roasted, dried, fermented, smoked and/or boiled meat, bone, cartilage, fish, vegetables, fruit, herbs, nuts, vegetable or fruit juices or pastes or mixtures thereof, digestible or non-digestible carbohydrates (e.g. sucrose, maltose, fructose, glucose, dextrins, amylose, amylopectin, inulin, xylans, cellulose, tagatose), sugar alcohols (e.g. sorbitol, erythritol), natural or hydrogenated fats (e.g. tallow, lard, palm fat, coconut fat, hydrogenated plant fat), oils (e.g. sunflower oil, groundnut oil, maize germ oil, olive oil, fish oil, soya oil, sesame oil), fatty acids or salts thereof (e.g. potassium stearate), proteinogenic or non-proteinogenic amino acids and related compounds (e.g. γ-aminobutyric acid, taurine), peptides (e.g. glutathione), native or processed proteins (e.g. gelatine), enzymes (e.g. peptidases), nucleic acids, nucleotides, flavour correctants for unpleasant flavour impressions, further flavour modulators for further, as a rule not unpleasant flavour impressions, other flavour-modulating substances (e.g. inositol phosphate, nucleotides, such as guanosine monophosphate, adenosine monophosphate or other substances, such as sodium glutamate or 2-phenoxypropionic acid), emulsifiers (e.g. lecithins, diacylglycerols, gum arabic), stabilizers (e.g. carrageenan, alginate), preservatives (e.g. benzoic acid, sorbic acid), antioxidants (e.g. tocopherol, ascorbic acid), chelating agents (e.g. citric acid), organic or inorganic acidifying agents (e.g. malic acid, acetic acid, citric acid, tartaric acid, phosphoric acid), bitter principles (e.g. quinine, caffeine, limonin, amarogentin, humulones, lupolones, catechols, tannins), mineral salts (e.g. sodium chloride, potassium chloride, magnesium chloride, sodium phosphates), substances which prevent enzymatic browning (e.g. sulfite, ascorbic acid), essential oils, plant extracts, natural or synthetic dyestuffs or coloured pigments (e.g. carotenoids, flavonoids, anthocyans, chlorophyll and derivatives thereof), spices, substances having a trigeminal action or plant extracts comprising such substances having a trigeminal action, synthetic, natural or nature-identical aroma substances or odoriferous substances and flavour correctants.

Dental care compositions (formulations according to the invention which serve as a basis for oral care) which comprise the 4-methyl-delta-hexylactone to be employed according to the invention or an odoriferous or aroma substance compositions according to the invention comprising 4-methyl-delta-hexylactone in general comprise an abrasive system (abrasive or polishing agent), such as e.g. silicas, calcium carbonates, calcium phosphates, aluminium oxides and/or hydroxyapatites, surface-active substances, such as e.g. sodium lauryl sulfate, sodium lauryl sarcosinate and/or cocamidopropylbetaine, moisture-retaining agents, such as e.g. glycerol and/or sorbitol, thickeners, such as e.g. carboxymethylcellulose, polyethylene glycols, carrageenan and/or Laponite®, sweeteners, such as e.g. saccharin, flavour correctants for unpleasant flavour impressions, flavour correctants for further, as a rule not unpleasant flavour impressions, flavour-modulating substances (e.g. inositol phosphate, nucleotides, such as guanosine monophosphate, adenosine monophosphate or other substances, such as sodium glutamate or 2-phenoxypropionic acid), cooling active compounds, such as e.g. menthol derivatives (e.g. L-menthyl lactate, L-menthyl alkyl carbonates, menthone ketals, menthanecarboxylic acid amides), 2,2,2-trialkylacetic acid amides (e.g. 2,2-diisopropylpropionic acid methylamide), icilin and icilin derivatives, stabilizers and active compounds, such as e.g. sodium fluoride, sodium monofluorophosphate, tin difluoride, quaternary ammonium fluorides, zinc citrate, zinc sulfate, tin pyrophosphate, tin dichloride, mixtures of various pyrophosphates, triclosan, cetylpyridinium chloride, aluminium lactate, potassium citrate, potassium nitrate, potassium chloride, strontium chloride, hydrogen peroxide, aromas and/or sodium bicarbonate or smell correctants.

Chewing gums (as a further example of formulations according to the invention for oral care) which comprise the 4-methyl-delta-hexylactone to be employed according to the invention or an odoriferous or aroma substance composition according to the invention comprising 4-methyl-delta-hexylactone in general comprise a chewing gum base, i.e. a chewing composition which becomes plastic on chewing, various types of sugars, sugar substitutes, other sweet-tasting substances, sugar alcohols (in particular sorbitol, xylitol, mannitol), cooling active compounds, flavour correctants for unpleasant flavour impressions, other flavour modulators for further, as a rule not unpleasant flavour impressions, flavour-modulating substances (e.g. inositol phosphate, nucleotides, such as guanosine monophosphate, adenosine monophosphate or other substances, such as sodium glutamate or 2-phenoxypropionic acid), moisture-retaining agents, thickeners, emulsifiers, aromas and stabilizers or smell correctants.

Numerous different chewing gum bases are known in the prior art, a distinction being made between so-called chewing gum—or bubble gum—bases, the latter being softer and it therefore also being possible to form chewing gum bubbles therewith. The usual chewing gum bases nowadays usually comprise, in addition to natural resins traditionally employed or the natural latex chicle, elastomers, such as polyvinyl acetates (PVA), polyethylenes, (low or medium molecular weight) polyisobutenes (PIB), polybutadienes, isobutene/isoprene copolymers (butyl rubber), polyvinyl ethyl ethers (PVE), polyvinyl butyl ethers, copolymers of vinyl esters and vinyl ethers, styrene/butadiene copolymers (styrene/butadiene rubber, SBR) or vinyl elastomers, e.g. based on vinyl acetate/vinyl laurate, vinyl acetate/vinyl stearate or ethylene/ vinyl acetate, and mixtures of the elastomers mentioned, as described, for example, in EP 0 242 325, U.S. Pat. No. 4,518,615, U.S. Pat. No. 5,093,136, U.S. Pat. No. 5,266,336 U.S. Pat. No. 5,601,858 or U.S. Pat. No. 6,986,709. In addition, chewing gum bases comprise further constituents, such as, for example, (mineral) fillers, plasticizers, emulsifiers, antioxidants, waxes, fats or fatty oils, such as, for example, hardened (hydrogenated) plant or animal fats, mono-, di- or triglycerides. Suitable (mineral) fillers are, for example, calcium carbonate, titanium dioxide, silicon dioxide, talc, aluminium oxide, dicalcium phosphate, tricalcium phosphate, magnesium hydroxide and mixtures thereof. Suitable plasticizers or agents for preventing sticking (detackifiers) are, for example, lanolin, stearic acid, sodium stearate, ethyl acetate, diacetin (glycerol diacetate), triacetin (glycerol triacetate), triethyl citrate. Suitable waxes are, for example, paraffin waxes, candelilla wax, carnauba wax, microcrystalline waxes and polyethylene waxes. Suitable emulsifiers are, for example, phosphatides, such as lecithin, mono- and diglycerides of fatty acids, e.g. glycerol monostearate.

The invention is explained in more detail in the following with the aid of examples. Unless stated otherwise, all the data relate to the weight.

Example 1

Preparation of 4-methyl-delta-hexylactone

The following equation illustrates the reaction sequence used here:

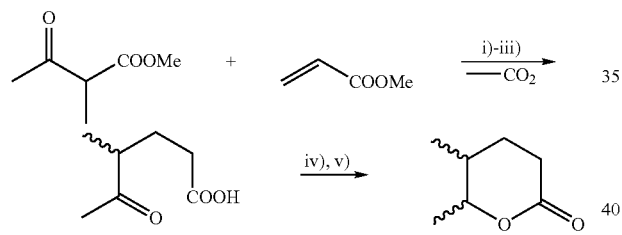

i) NaOMe/MeOH, ii) KOH/H$_2$O; iii) H$_2$SO$_4$/H$_2$O; iv) NaBH$_4$, v) H$_2$SO$_4$ A solution of 7.5 g (0.14 mol) sodium methylate (95% pure) in 30 ml anhydrous methanol was added dropwise to 402 g (2.8 mol) 2-methylacetoacetic acid methyl ester (98% pure), with vigorous stirring and starting at room temperature (approx. 20° C.); 225 g (2.6 mol) acrylic acid methyl ester were then added dropwise to this mixture at 30° C. (internal temperature), while stirring. The reaction mixture obtained was stirred for 15 h at room temperature and then added dropwise to a solution of 360 g (5.5 mol) potassium hydroxide (85% pure) in 100 ml water and 700 ml methanol, and the mixture was stirred for 12 h at room temperature and subsequently acidified with a solution of 300 g concentrated sulfuric acid (96% strength) in 400 ml water, while cooling in an ice-bath. The resulting mixture was concentrated in vacuo (20 mbar/40° C. bath temperature), and the residue was diluted with 1,500 ml water and then extracted four times with 400 ml ether each time. The combined ether extracts were concentrated in vacuo (20 mbar/40° C. bath temp.). The residue which remained here (363 g) was now added dropwise to a solution of 170 g (2.58 mol) potassium hydroxide (85% pure) in 1,400 ml water, a solution of 2 g 50% strength aqueous sodium hydroxide solution and 24 g (0.64 mol) sodium boranate in 100 ml water was then added dropwise at room temperature, and the resulting reaction mixture was stirred for 12 h at room temperature, acidified with 90 g (0.9 mol) concentrated sulfuric acid (96% strength) and extracted four times with 400 ml ether each time. The combined ether extracts were concentrated in vacuo (20 mbar, 40° C. bath temp.) and the residue obtained was then subjected to fractional distillation in vacuo over a 50 cm Vigreux column. At an overhead temperature of 59-60° C./0.76 mbar, 131 g of the product of the formula A (according to GC a 1:1 mixture of the two syn and anti diastereomers) were obtained as a colourless liquid (purity according to GC: 98.6%, sum of the two diastereomers).

1H-NMR (400 MHz/CDCl$_3$/TMS): 0.98 (d, 4-CH$_3$, J=6.95 Hz, diastereomer 1), 1.01 (d, 4-CH$_3$, J=6.47 Hz, diastereomer 2), 1.30 (d, CH$_3$, J=6.66 Hz, diastereomer 1), 1.37 (d, CH$_3$, J=6.26 Hz, diastereomer 2), 1.50-1.74 (m, 3-CH$_2$, both diastereomers), 1.88-2.10 (m, 4-CH, both diastereomers), 2.46-2.66 (m, 2-CH$_2$, both diastereomers), 4.03-4.09 (m, 5-CH, diastereomer 1), 4.52-4.56 ppm (m, 5-CH, diastereomer 2).

13C-NMR (75 MHz/CDCl$_3$/TMS): 13.06 (q, 4-CH$_3$, diastereomer 1), 17.30 (q, CH$_3$, diastereomer 1 and 4-CH$_3$, diastereomer 2), 19.97 (q, CH$_3$, diastereomer 2), 25.37 (t, 3-CH$_2$, diastereomer 1), 27.05 (t, 2-CH$_2$, diastereomer 1), 27.78 (t, 3-CH$_2$, diastereomer 2), 29.62 (t, 2-CH$_2$, diastereomer 2), 30.37 (d, 4-CH, diastereomer 1), 34.59 (d, 4-CH, diasteromer 2), 79.09 (d, 5-CH, diastereomer 1), 82.43 (d, 5-CH, diastereomer 2), 171.79 ppm (s, C=O, diastereomer 1 and 2).

FT-IR: 1097 (m), 1250 (m), 1257 (m), 1730 (s), 2879 (m), 2937 (m), 2974 1/cm (m).

MS (70 MeV) m/z=128 (2.4%, M+), 84 (36%, M-CO$_2$), 56 (100%), 43 (28%), 42 (37%), 41 (26%).

Example 2

Aroma Substance Compositions (Synthetic Peppermint Oils)

| | Aroma P parts by weight | Aroma A1 parts by weight | Aroma A2 parts by weight |
|---|---|---|---|
| Isobutyraldehyde | 0.5 | 0.5 | 0.5 |
| 3-Octanol | 0.5 | 0.5 | 0.5 |
| Dimethyl sulfide | 0.5 | 0.5 | 0.5 |
| trans-2-Hexenal | 1.0 | 1.0 | 1.0 |
| cis-3-Hexenol | 1.0 | 1.0 | 1.0 |
| 4-Terpineol, natural | 1.0 | 1.0 | 1.0 |
| Isopulegol | 1.0 | 1.0 | 1.0 |
| Piperitone, natural, from eucalyptus | 2.0 | 2.0 | 2.0 |
| Linalool | 3.0 | 3.0 | 3.0 |
| 8-Ocimenyl acetate, 10% in triacetin | 5.0 | 5.0 | 5.0 |
| Isoamyl alcohol | 10.0 | 10.0 | 10.0 |
| Isovaleraldehyde | 10.0 | 10.0 | 10.0 |
| alpha-Pinene | 25.0 | 25.0 | 25.0 |
| beta-Pinene, natural | 25.0 | 25.0 | 25.0 |
| Neomenthol, racemic | 40.0 | 40.0 | 40.0 |
| Eucalyptol (1,8-cineol), natural | 50.0 | 50.0 | 50.0 |
| L-Menthyl acetate of the formula D | 70.0 | 70.0 | 70.0 |
| L-Menthone | 220.0 | 220.0 | 220.0 |
| D-Isomenthone | 50.0 | 50.0 | 50.0 |
| L-Menthol | 482.5 | 482.5 | 482.5 |
| 4-Methyl-delta-hexalactone of the formula A, from Example 1 | — | 1.0 | 1.0 |
| Nonenolide of the formula C, racemic | — | — | 1.0 |
| Total: | 998.0 | 999.0 | 1000.0 |

In the opinions of the flavourists, aroma P (not according to the invention), a non-natural reconstruction of a peppermint oil, acquires a note of hay and coumarin by the addition of 1 part by weight of 4-methyl-delta-hexylactone (aroma A1), 4-Methyl-delta-hexylactone blends well into the composition, imparts to the composition more naturalness and authenticity and rounds this off. These notes and effects are intensified more by the further addition of 1 part by weight of nonenolide (aroma A2).

FORMULATION EXAMPLES

Example F1

Gel Dental Cream Having an Activity Against Bad Breath

|  | I (wt. %) | II (wt. %) | III (wt. %) |
|---|---|---|---|
| Na carboxymethylcellulose | 0.40 | 0.40 | 0.40 |
| Sorbitol 70%, in water | 72.00 | 72.00 | 72.00 |
| Polyethylene glycol (PEG) 1500 | 3.00 | 3.00 | 3.00 |
| Na saccharinate | 0.07 | 0.07 | 0.07 |
| Na fluoride | 0.24 | 0.24 | 0.24 |
| p-Hydroxybenzoic acid (PHB) ethyl ester | 0.15 | 0.15 | 0.15 |
| Aroma A1 from Example 2 | 0.50 | 0.80 | 1.50 |
| Abrasive silica | 11.00 | 11.00 | 11.00 |
| Thickening silica | 6.00 | 6.00 | 6.00 |
| Sodium dodecyl sulfate (SDS) | 1.40 | 1.40 | 1.40 |
| Dist. water | to 100.00 | to 100.00 | to 100.00 |

Example F2

Dental Cream Against Plaque

|  | I (wt. %) | II (wt. %) | III (wt. %) |
|---|---|---|---|
| Na carboxymethylcellulose | 1.00 | 1.00 | 1.00 |
| Glycerol | 12.50 | 12.50 | 12.50 |
| Sorbitol 70%, in water | 29.00 | 29.00 | 29.00 |
| Na saccharinate | 0.20 | 0.20 | 0.20 |
| Na fluoride | 0.22 | 0.22 | 0.22 |
| Azacycloheptane-2,2-diphospho acid, di-sodium salt | 1.00 | 1.00 | 1.00 |
| Bromochlorophene | 0.10 | 0.10 | 0.10 |
| Aroma A2 from Example 2 | 0.15 | 0.90 | 1.20 |
| Abrasive silica | 15.00 | 15.00 | 15.00 |
| Thickening silica | 5.00 | 5.00 | 5.00 |
| Sodium dodecyl sulfate (SDS) | 1.50 | 1.50 | 1.50 |
| Dist. water | to 100.00 | to 100.00 | to 100.00 |

Example F3

Dental Cream Against Plaque

|  | I (wt. %) | II (wt. %) | III (wt. %) |
|---|---|---|---|
| Carrageenan | 0.90 | 0.90 | 0.90 |
| Glycerol | 15.00 | 15.00 | 15.00 |
| Sorbitol 70%, in water | 25.00 | 25.00 | 25.00 |
| PEG 1000 | 3.00 | 3.00 | 3.00 |
| Na fluoride | 0.24 | 0.24 | 0.24 |
| Tetrapotassium diphosphate | 4.50 | 4.50 | 4.50 |
| Tetrasodium diphosphate | 1.50 | 1.50 | 1.50 |
| Na saccharinate | 0.40 | 0.40 | 0.40 |
| Precipitated silica | 20.00 | 20.00 | 20.00 |
| Titanium dioxide | 1.00 | 1.00 | 1.00 |
| PHB methyl ester | 0.10 | 0.10 | 0.10 |
| Anethole-eucalyptol aroma | 0.10 | 0.25 | 0.20 |
| Aroma A1 from Example 2 | 0.50 | 0.70 | 1.00 |
| Sodium dodecyl sulfate | 1.30 | 1.30 | 1.30 |
| Dist. water | to 100.00 | to 100.00 | to 100.00 |

Example F4

Dental Cream Against Sensitive Teeth

|  | I (wt. %) | II (wt. %) | III (wt. %) |
|---|---|---|---|
| Na carboxymethylcellulose | 0.70 | 0.70 | 0.70 |
| Xanthan Gum | 0.50 | 0.50 | 0.50 |
| Glycerol | 15.00 | 15.00 | 15.00 |
| Sorbitol 70%, in water | 12.00 | 12.00 | 12.00 |
| K nitrate | 5.00 | 5.00 | 5.00 |
| Na monofluorophosphate | 0.80 | 0.80 | 0.80 |
| PHB methyl ester | 0.15 | 0.15 | 0.15 |
| PHB propyl ester | 0.05 | 0.05 | 0.05 |
| Na saccharinate | 0.20 | 0.20 | 0.20 |
| Wintergreen aroma (contains methyl salicylate) | 0.05 | 0.15 | 0.10 |
| Aroma A1 from Example 2 | 0.25 | 0.65 | 1.10 |
| Ca carbonate | 35.00 | 35.00 | 35.00 |
| Silicon dioxide | 1.00 | 1.00 | 1.00 |
| Sodium dodecyl sulfate (SDS) | 1.50 | 1.50 | 1.50 |
| Dist. water | to 100.00 | to 100.00 | to 100.00 |

Example F5

Dental Cream Against Sensitive Teeth

|  | I (wt. %) | II (wt. %) | III (wt. %) |
|---|---|---|---|
| Hydroxyethylcellulose | 1.40 | 1.40 | 1.40 |
| Guar gum | 0.60 | 0.60 | 0.60 |
| Glycerol | 18.00 | 18.00 | 18.00 |
| Sorbitol 70%, in water | 12.00 | 12.00 | 12.00 |
| Na saccharinate | 0.35 | 0.35 | 0.35 |
| Dyestuff | 0.01 | 0.01 | 0.01 |
| PHB methyl ester | 0.15 | 0.15 | 0.15 |
| PHB propyl ester | 0.04 | 0.04 | 0.04 |
| Sr chloride | 10.50 | 10.50 | 10.50 |
| Aroma A2 from Example 2 | 0.40 | 1.00 | 1.50 |
| Precipitated silica | 15.00 | 15.00 | 15.00 |
| Silicon dioxide | 1.60 | 1.60 | 1.60 |
| Sodium dodecyl sulfate | 1.30 | 1.30 | 1.30 |
| Dist. water | to 100.00 | to 100.00 | to 100.00 |

Example F6

Ready-to-Use Mouthwash with Fluoride

|  | I (wt. %) | II (wt. %) | III (wt. %) |
|---|---|---|---|
| Ethanol | 7.00 | 7.00 | 7.00 |
| Glycerol | 12.00 | 12.00 | 12.00 |
| Na fluoride | 0.05 | 0.05 | 0.05 |
| Pluronic F-127 ® (BASF, surface-active substance) | 1.40 | 1.40 | 1.40 |
| Na phosphate buffer pH 7.0 | 1.10 | 1.10 | 1.10 |
| Sorbic acid | 0.20 | 0.20 | 0.20 |
| Na saccharinate | 0.10 | 0.10 | 0.10 |
| Aroma A2 from Example 2 | 0.10 | 0.25 | 0.40 |
| Dyestuff | 0.01 | 0.01 | 0.01 |
| Dist. water | to 100.00 | to 100.00 | to 100.00 |

Example F7

Mouthwash Concentrate

|  | I (wt. %) | II (wt. %) | III (wt. %) |
|---|---|---|---|
| Ethanol, 95% strength | 80.00 | 80.00 | 80.00 |
| Na cyclamate | 0.15 | 0.15 | 0.15 |
| Eucalyptol aroma (contains natural eucalyptol) | 1.00 | 1.00 | 1.00 |
| Dyestuff | 0.01 | 0.01 | 0.01 |
| Aroma A1 from Example 2 | 2.00 | 3.00 | 4.00 |
| Dist. water | to 100.00 | to 100.00 | to 100.00 |

Example F8

Sugar-Containing Chewing Gums

|  | I (wt. %) | II (wt. %) | III (wt. %) |
|---|---|---|---|
| Chewing gum base | 21.00 | 21.00 | 21.00 |
| Glucose syrup | 16.50 | 16.50 | 16.50 |
| Glycerol | 0.50 | 0.50 | 0.50 |
| Powdered sugar | 60.45 | 60.40 | 60.30 |
| Encapsulated wintergreen aroma (contains methyl salicylate) | 1.20 | 1.00 | 0.70 |
| Aroma A2 from Example 2 | 0.35 | 0.60 | 1.00 |

Examples F9a-9d

Sugar-Free Chewing Gums

Example F9a

Non-Stick Chewing Gum

Chewing gum base K1 comprised 2.0% butyl rubber (isobutene/isoprene copolymer, MW 400,000), 6.0% polyisobutene (MW=43,800), 43.5% polyvinyl acetate (MW=12,000), 31.5% polyvinyl acetate (MW=47,000), 6.75% triacetin and 10.25% calcium carbonate. Chewing gum base K1 and the chewing gums can be prepared analogously to U.S. Pat. No. 5,601,858.

|  | I (wt. %) | II (wt. %) | III (wt. %) |
|---|---|---|---|
| Chewing gum base K1 | 26.00 | 26.00 | 26.00 |
| Triacetin | 0.25 | 0.25 | 0.25 |
| Lecithin | 0.50 | 0.50 | 0.50 |
| Sorbitol, crystalline | 40.90 | 40.60 | 40.50 |
| Mannitol | 15.30 | 15.20 | 15.10 |
| Glycerol | 12.10 | 12.00 | 11.80 |
| Aspartame | 0.17 | 0.17 | 0.17 |
| Encapsulated aspartame | 1.08 | 1.08 | 1.08 |
| Amorphous silica | 1.00 | 1.00 | 1.00 |
| Cottonseed oil | 0.50 | 0.50 | 0.50 |
| Polyoxyethylene sorbitan monolaurate (E-432) | 1.00 | 1.00 | 1.00 |
| Encapsulated spearmint aroma (contains I-carvone) | 0.20 | 0.10 | 0.20 |
| Encapsulated wintergreen aroma (contains methyl salicylate) | — | 0.20 | — |
| Aroma A1 from Example 2 | 1.00 | 1.40 | 1.70 |
| I-Menthyl I-lactate | 0.10 | — | 0.20 |

Example F9b

Bubble Gum

The bubble gum can be prepared analogously to U.S. Pat. No. 5,093,136.

|  | I (wt. %) | II (wt. %) |
|---|---|---|
| Styrene/butadiene copolymer (SBR) | 19.50 | 17.50 |
| Polyisobutene | 8.00 | 8.00 |
| Sorbitol powder | 49.19 | 47.19 |
| Sorbitol, 70%, in water | 9.20 | 22.20 |
| Hydrogenated starch hydrolysates (HSH) | 9.00 | — |
| Glycerol | 3.00 | 2.00 |
| Aspartame | 0.10 | 0.10 |
| Encapsulated aspartame | 0.50 | 0.50 |
| Green and blue dyestuff | 0.01 | 0.01 |
| Aroma A2 from Example 2 | 1.50 | 2.50 |

The chewing gums of recipe (I) were shaped as compact balls, and those of recipe (II) were shaped as hollow balls.

Example F9c

Chewing gum base K2 comprised 28.5% terpene resin, 33.9% polyvinyl acetate (MW=14,000), 16.25% hydrogenated plant oil, 5.5% mono- and diglycerides, 0.5% polyisobutene (MW 75,000), 2.0% butyl rubber (isobutene/isoprene copolymer), 4.6% amorphous silicon dioxide (water content approx. 2.5%), 0.05% antioxidant tert-butylhydroxytoluene (BHT), 0.2% lecithin, and 8.5% calcium carbonate. Chewing gum base K2 and the chewing gums can be prepared analogously to U.S. Pat. No. 6,986,907.

|  | I (wt. %) | II (wt. %) | III (wt. %) |
|---|---|---|---|
| Chewing gum base K2 | 25.30 | 27.30 | 26.30 |
| Sorbitol | 61.48 | 59.48 | 61.80 |
| Glycerol | 2.40 | 2.40 | 2.40 |
| Lecithin | 7.00 | 7.00 | 7.00 |
| Aspartame | 0.14 | 0.14 | 0.14 |
| Encapsulated aspartame | 0.68 | 0.68 | 0.68 |
| Menthol, spray-dried | 0.50 | — | — |

-continued

|  | I (wt. %) | II (wt. %) | III (wt. %) |
|---|---|---|---|
| Cherry aroma, spray-dried | — | 1.20 | — |
| Aroma A1 from Example 2, spray-dried | 1.50 | 1.80 | — |
| Aroma A2 from Example 2 | 1.00 | — | 1.68 |

The chewing gums of recipe (I) and (II) were shaped as strips, and those of recipe (III) were shaped as pellets.

Example F9d

|  | I (wt. %) | II (wt. %) | III (wt. %) |
|---|---|---|---|
| Chewing gum base | 30.00 | 30.00 | 30.00 |
| Sorbitol, powder | 38.45 | 38.40 | 38.30 |
| Palatinite | 9.50 | 9.50 | 9.50 |
| Xylitol | 2.00 | 2.00 | 2.00 |
| Mannitol | 3.00 | 3.00 | 3.00 |
| Aspartame | 0.10 | 0.10 | 0.10 |
| Acesulfame K | 0.10 | 0.10 | 0.10 |
| Emulgum/emulsifier | 0.30 | 0.30 | 0.30 |
| Sorbitol 70%, in water | 14.00 | 14.00 | 14.00 |
| Glycerol | 1.00 | 1.00 | 1.00 |
| Aniseed-cinnamon aroma | 1.10 | 0.60 | 0.50 |
| Aroma A1 from Example 2 | 0.45 | 0.80 | 1.00 |
| l-Menthyl l-lactate | — | 0.20 | 0.10 |
| 2-Hydroxypropyl menthyl carbonate | — | — | 0.10 |

Example F10

Gelatine Capsule for Direct Consumption

|  | I (wt. %) | II (wt. %) | III (wt. %) |
|---|---|---|---|
| Gelatine shell: |  |  |  |
| Glycerol | 2.014 | 2.014 | 2.014 |
| Gelatine 240 Bloom | 7.91 | 7.91 | 7.91 |
| Sucralose | 0.065 | 0.065 | 0.065 |
| Allura Red | 0.006 | 0.006 | 0.006 |
| Brilliant Blue | 0.005 | 0.005 | 0.005 |
| Core composition: |  |  |  |
| Plant oil triglyceride (coconut oil fraction) | 79.39 | 68.40 | 58.25 |
| Aroma A2 from Example 2 | 10.0 | 20.0 | 28.65 |
| Neotame and aspartame | 0.01 | 0.05 | — |
| Sucralose | 0.22 | 0.30 | 0.70 |
| 2-Hydroxypropyl menthyl carbonate | 0.33 | 0.20 | — |
| 2-Hydroxyethyl menthyl carbonate | — | 0.20 | 1.00 |
| (1R,3R,4S) Menthyl-3-carboxylic acid N-ethylamide (WS-3) | — | 0.55 | 0.50 |
| (—)-Menthone glycerol acetal (Frescolat MGA) | — | 0.30 | 0.80 |
| Vanillin | 0.05 | — | 0.10 |

The gelatine capsule, which is suitable for direct consumption, was prepared in accordance with WO 2004/050069 and had a diameter of 5 mm, and the weight ratio of core material to shell material was 90:10. The capsules opened in the mouth within less than 10 seconds and dissolved completely within less than 50 seconds.

Example F11

Bonbon for Chewing with Aroma According to the Invention

| Water |  | 7.8% |
|---|---|---|
| Sugar | refined sugar C4 | 42.1% |
| Glucose syrup | dextrose 40 | 37.3% |
| Hydrogenated plant fat | melting point 32-36° C. | 6.6% |
| Lecithin | emulsifier (soya lecithin) | 0.3% |
| Gelatine | pig gelatine | 0.8% |
| Fondant | type S30 | 4.9% |
| Aroma A1 from Example 2 |  | 0.2% |

Preparation instructions:
a) Swell the gelatine with water (1.8 times the amount of gelatine) at 70° C. for 2 hours;
b) boil the sugar, syrup, water, fat and lecithin at 123° C.;
c) slowly mix the gelatine solution with the boiling mixture;
d) stir in the aroma from Example 2 and optionally colour;
e) control the resulting mass at a temperature of approx. 70° C. on a cooling table, then add the fondant and aerate on a drawing machine for approx. 3 minutes;
f) subsequently cut the bonbon for chewing mass and package.

When the bonbon for chewing is consumed, a strong peppermint flavour is perceived during the chewing.

Example F12

Compressed Tablets with Aroma According to the Invention

| Dextrose | 98.0 wt. % |
|---|---|
| Magnesium stearate (lubricant) | 0.9 wt. % |
| Citric acid | 0.3 wt. % |
| Aroma A2 from Example 2 | 0.8 wt. % |

Preparation instructions: Mix all the constituents and press to compressed tablets in a suitable machine.

Example F13

Fool with Aroma According to the Invention

| Sugar | sucrose | 81.9 wt. % |
|---|---|---|
| Stabilizer | Hamulsion GGF Hahn & Co., Lübeck | 12.0 wt. % |
| Citric acid | ground | 3.0 wt. % |
| Trisodium citrate | gelling aid | 2.0 wt. % |
| Green colour |  | 0.05 wt. % |
| Aroma A1 from Example 2 |  | 1.05 wt. % |

Preparation instructions: Stir 41 g of this mixture into 250 ml of boiling water and allow to cool.

Example F14

Extrudate with Aroma According to the Invention

| | | |
|---|---|---|
| Glucose syrup, spray-dried (DE value: 31-34) | Glucidex IT33W (Roquette) | 62.0% |
| Maltodextrin (DE value: 17-20) | (Cerestar) | 28.4% |
| Emulsifier Monomuls | emulsifier based on hydrogenated palm oil; melting point: 64° C., (Grünau) | 1.8% |
| Dextrose monohydrate (DE value: 99.5) | dextrose, containing water of crystallization (Cerestar) | 1.8% |
| Water | | 2.0% |
| Aroma A2 from Example 2 | | 4.0% |

Preparation instructions (see also WO 03/092412):

All the constituents were mixed and the mixture was conveyed in a twin-screw extruder by one-point metering. The extrusion temperatures were between 100 and 120° C. and the specific energy input was 0.2 kWh/kg. The strands emerging from the extruder die plate, which was provided with 1 mm bores, were cut to particles of approx. 1 mm diameter by rotating blades immediately after exit from the dies.

Example F15

Fluidized Bed Granules with Aroma According to the Invention

A solution consisting of 44 wt. % water, 11 wt. % aroma A1 according to the invention from Example 2, 13 wt. % gum arabic and 32 wt. % hydrolysed starch (maltodextrin DE 15-19) and some green dyestuff is granulated in a granulating apparatus of the type described in EP 163 836 (with the following features: diameter of in-flow tray: 225 mm, spray nozzle: two-component nozzle; sifting discharge: zigzag sifter; filter: internal bag filter). The solution is sprayed into the fluidized bed granulator at a temperature of 32° C. To fluidize the contents of the bed, an amount of 140 kg/h of nitrogen is blown in. The entry temperature of the fluidizing gas is 140° C. The temperature of the waste gas is 76° C. Nitrogen is likewise fed in as the sifting gas in an amount of 15 kg/h at a temperature of 50° C. The contents of the fluidized bed is approx. 500 g. The granulation output is approx. 2.5 kg per hour. Free-flowing granules having an average particle diameter of 360 micrometers are obtained. The granules are circular and have a smooth surface. On the basis of the constant pressure loss of the filter and the content of the bed, which likewise remains constant, stationary conditions are to be assumed in respect of the granulation process.

Example F16

Tea-Bag with Black Tea or Rooibos Tea and Granules Comprising Aroma According to the Invention

Example F16a 800 g of Red Bush Tea (rooibos tea) and 33 g of the aroma particles from Example F14 comprising aroma A2 according to the invention from Example 2 were mixed and the mixture was divided into portions and transferred into tea-bags.

Example F16b 850 g of black tea fannings were initially introduced into a 5 liter Lödige ploughshare mixer and premixed and fluidized for 10 seconds. Without interruption of the mixing process, 6 g of a fine neutral oil mist (medium chain triglycerides oil aerosol) were sprayed on to the fluidized tea leaves by means of a one- or two-component nozzle. This lasted about 60 seconds. Without interruption of the mixing process, 40 g of the abovementioned coloured aroma particles from Example F15 comprising aroma A1 according to the invention from Example 2 were then added to the fluidized mixture and the entire mixture was mixed for a further 60 seconds. The mixture obtained in this way was then divided into portions and transferred into tea-bags.

Example F17

Chewing Gum Dragées, Sugar-Free

Q1: Chewing Gum Base Composition Constituents

| | I (wt. %) | II (wt. %) | III (wt. %) |
|---|---|---|---|
| Chewing gum base | 37.00 | 37.00 | 37.00 |
| Sorbitol, powder | 50.50 | 50.50 | 50.50 |
| Aspartame | 0.20 | 0.20 | 0.20 |
| Plasticizer (Emulgum) | 0.50 | 0.50 | 0.50 |
| Acesulfame K | 0.20 | 0.20 | 0.20 |
| Sorbitol 70% strength in water | 5.00 | 5.00 | 5.00 |
| Glycerol | 4.00 | 4.00 | 4.00 |
| Aroma A1 from Example 2 | 1.20 | 1.40 | 1.60 |
| Peppermint oil aroma (Optamint ®, Symrise) | 0.40 | 0.20 | — |
| Menthol, crystalline | 1.00 | 0.50 | 0.10 |
| Menthol, spray-dried | — | 0.50 | 0.90 |

Q2: Coating Constituents (Covering)
(the weight contents stated relate to the total weight of the coating (Q2) applied to the chewing gum pads (Q1); the total weight of Q2 was about 35%, based on the weight of Q1)

| | I (wt. %) | II (wt. %) | III (wt. %) |
|---|---|---|---|
| Mixture A | | | |
| Isomaltol | 0.20 | 0 | 0 |
| Sorbitol | 0 | 0.40 | 0 |
| Mannitol | 0 | 0 | 0.80 |
| I-Menthol, spray-dried | 0.20 | 0.60 | 1.00 |
| Mixture B | | | |
| Isomaltol | 68.00 | 67.70 | 67.40 |
| Water | 26.7 | 26.6 | 26.5 |
| Gum arabic 40% strength in water (this content includes the amount used for the gumming) | 2.50 | 2.50 | 2.50 |
| Acesulfame K | 0.05 | 0.05 | 0.05 |
| Aspartame | 0.05 | 0.05 | 0.05 |
| Titanium dioxide | 1.50 | 1.50 | 1.50 |
| Constituent C | | | |
| Aroma A2 from Example 2 | 0.80 | 0.60 | 0.20 |

All the constituents of the chewing gum base composition (Q1) were mixed, stamped into chewing gum strands and then shaped into individual chewing gum pads. The chewing gum pads were then wetted (gummed) with a 40 wt. % strength gum arabic solution in a rotating dragée-coating drum. The gummed chewing gum pads were then coated in a rotating dragée-coating drum with the pulverulent mixture A, which substantially comprised spray-dried 1-menthol and at least one sugar substitute (usually chosen from isomaltol, sorbitol, xylitol, maltitol and/or mannitol, pulverulent gum arabic can optionally additionally be used). After adequate drying with cold air, the chewing gum pads coated in this way were dried overnight. For further application of the coating to the dried, coated chewing gum pads using coating solution B, 15 layers were first applied by means of dragée-coating, and in the 16th layer a mixture of constituent C and mixture B was applied. Thereafter, further layers were applied using mixture B, until the total weight of the coating (Q2) was about 35 wt. % of the weight of the original chewing gum pads (Q1). In order to impart gloss to the chewing gum dragées, a final treatment was carried out with a polishing agent, which comprised a mixture of equal weight contents of carnauba wax and beeswax. The ready-to-use chewing gum dragées cause a very clear, radiant, fresh mentholic and natural peppermint flavour during chewing in the mouth.

Example F18

Spray-Dried Aroma According to the Invention

A spray-dried aroma according to the invention coloured green-yellow (comprising maltodextrin (DE: 18-20), dextrose, gum arabic, aroma A1 from Example 2, (−)-carvone, dyestuff and the antioxidant ascorbyl palmitate) with the following particle size distribution was prepared via a pressure nozzle:

D (v 0.1): 26.8 micrometers,

D (v 0.5): 68.02 micrometers,

D (v 0.9): 126.4 micrometers

Example F19

Instant Drink Powder with Spray-Dried Aroma According to the Invention

| | |
|---|---|
| Sugar (sucrose) | 82.249 wt. % |
| Citric acid | 11.58 wt. % |
| Trisodium citrate | 0.70 wt. % |
| Tricalcium phosphate | 0.60 wt. % |
| Vitamin C | 0.66 wt. % |
| Grindsted ® JU 543 Stabilizer System (Danisco) | 0.90 wt. % |
| Saccharin | 0.561 wt. % |
| Lemon aroma, spray-dried | 1.75 wt. % |
| Aroma, spray-dried, according to Example F18 | 1.00 wt. % |

45 g of this instant drink powder were dissolved in 1,000 ml, while stirring. The drink obtained had a refreshing, cooling flavour of lemon and peppermint.

Example F20

Hard Caramel (Hard Boiled Candy) with Aroma According to the Invention

| | |
|---|---|
| Sugar (sucrose) | 51.89 wt. % |
| Maize syrup (corn syrup), contains glucose and fructose | 41.00 wt. % |
| Maltose | 3.00 wt. % |
| Palm kernel oil | 0.90 wt. % |
| Citric acid | 0.30 wt. % |
| Ginseng extract | 0.40 wt. % |
| Blue dyestuff | 0.01 wt. % |
| Aroma A2 from Example 2 | 2.50 wt. % |

The sugar, maize syrup and maltose were dissolved in water and the solution was boiled and placed under a vacuum. The remaining ingredients were then sucked into the boiled sugar mass and the mixture was homogenized at the boiling temperature. After cooling, hard caramels were stamped out of the resulting mass. The hard caramels showed a residual water content of about 2.5 wt. %.

Example F21

Throat Bonbons with a Liquid-Viscous Core Filling (Centre-Filled Hard Candy) with Aroma According to the Invention

| | I (wt. %) | II (wt. %) |
|---|---|---|
| Mixture A (shell) (80% of the bonbon) | | |
| Sugar (sucrose) | 58.12 | 49.37 |
| Glucose syrup (solids content 80%) | 41.51 | 49.37 |
| Aroma A1 from Example 2 | 0.17 | 0.25 |
| l-Menthol | 0.10 | — |
| Lemon oil | 0.10 | 0.10 |
| Citric acid | — | 0.91 |
| Total: | 100 | 100 |
| Mixture B (core) (20% of the bonbon) | | |
| High fructose maize syrup (content of solid sugars 85%, close to 15% water) | 84.38 | 84.36 |
| Glycerol | 15.0 | 15.0 |
| Lecithin | 0.02 | 0.02 |
| Cinnamon oil | — | 0.32 |
| Aroma A1 from Example 2 | 0.28 | — |
| Capsaicin | 0.05 | — |
| Vanillyl alcohol n-butyl ether | — | 0.10 |
| Red dyestuff, as a 5% strength aqueous solution | 0.20 | 0.20 |
| Vanillin | 0.07 | — |
| Total | 100 | 100 |

Bonbons having a liquid-viscous core were prepared in accordance with the processes described in U.S. Pat. No. 6,432,441 (Example 1 there) and in U.S. Pat. No. 5,458,894 and U.S. Pat. No. 5,002,791. The two mixtures A and B were processed separately to bases for the shell (mixture A) and core (mixture B). The filled throat bonbons obtained by means of co-extrusion acted against coughing, sore throat and hoarseness when consumed by affected persons.

Example F22

Liqueur with Aroma According to the Invention

A ready-to-consume alcoholic drink in the form of a liqueur tasting of peppermint was prepared by mixing 5 g of aroma A2 according to the invention from Example 2 and 100 liters of a green-coloured alcoholic-aqueous sugar solution which contained 18 wt. % sugar (sucrose) and 17.5 vol. % alcohol (ethanol).

Example F23

Refreshing Drink with Aroma According to the Invention

A ready-to-consume non-alcoholic drink in the form of a refreshing drink tasting of peppermint was prepared by mixing 1 g of aroma A2 according to the invention from Example 2 and 100 liters of a 10.8 wt. % strength sugar solution coloured yellow-green.

We claim:

1. A perfumed or aromatized article having a hay-like, coumaric note, said article comprising a mixture of:
   (a) 4-methyl-delta-hexylactone, and
   (b) at least one compound chosen from the group consisting of:
      (i) menthol,
      (ii) (−)-carvone
      (iii) menthone and
      (iv) isomenthone,
   where said 4-methyl-delta-hexylactone is present in an amount effective to impart the hay-like, coumaric note to said perfumed article or aromatized article and where said 4-methyl-delta-hexylactone by itself does not have a hay-like coumaric note.

2. An article according to claim 1, wherein said article is chosen from the group consisting of:
   an odoriferous or aroma substance composition,
   a formulation for nutrition,
   a formulation for oral care and
   a formulation for consumption for pleasure.

3. An article according to claim 1, comprising an amount of 4-methyl-delta-hexylactone which is sufficient to impart, modify and/or intensify one or more smell or flavour impressions.

4. An article according to claim 2, wherein the odoriferous or aroma substance composition comprises an amount of 4-methyl-delta-hexylactone in the range of 50 to 8,000 ppm, based on the total amount of said composition.

5. An article according to claim 1, comprising an amount of one or more compounds chosen from the group consisting of
   (i) menthol,
   (ii) (−)-carvone,
   (iii) menthone and
   (iv) isomenthone,
   which is sufficient to generate a dominant peppermint and/or spearmint smell or flavour note in said article.

6. An article according to claim 2, wherein the article is an odoriferous or aroma substance composition, comprising:
   (a) 4-methyl-delta-hexylactone in the range of 50 to 8,000 ppm, and
   (b) (i) menthol, in the range of 1 to 80 wt. %, and/or
      (ii) (−)-carvone in the range of 1 to 80 wt. %, and/or
      (iii) menthone, and/or
      (iv) isomenthone, in the range of 0.5 to 60 wt. %,
   wherein the amounts stated in each case are based on the total amount of said odoriferous or aroma substance composition.

7. A formulation for nutrition, oral care or consumption for pleasure, comprising a mixture comprising
   (a) 4-methyl-delta-hexylactone in an amount in the range of 0.05 to 80 ppm, and
   (b) at least one compound chosen from the group consisting of:
      (i) menthol,
      (ii) (−)-carvone
      (iii) menthone and
      (iv) isomenthone
   where the amount of said 4-methyl-delta-hexylactone imparts a hay-like, coumaric note to the formulation and where said 4-methyl-delta-hexylactone by itself does not have a hay-like, coumaric note.

8. A formulation according to claim 7, wherein said formulation is ready-to-use and is
   (A) a ready-to-consume confectionery, in the form of: a chocolate, filled chocolate, chocolate bar product, fruit gum, hard or soft caramel, bonbon for chewing, sugar bead, lollypop, capsule, or chewing gum, or
   (B) an oral care produce (oral hygiene product), in the form of: a toothpaste, dental cream, dental gel, dental powder, tooth-cleaning liquid, tooth-cleaning foam, mouthwash, dental cream and mouthwash as a 2-in-1 product, bonbon for sucking, oral spray, dental floss or dental care chewing gum, or
   (C) an alcoholic or non-alcoholic drink.

9. A process for the preparation of an odoriferous or aroma substance composition having a hay-like, coumaric note, comprising:
   mixing an odoriferous or aroma substance composition with
   (a) 4-methyl-delta-hexylactone, and
   (b) at least one compound chosen from the group consisting of:
      (i) menthol,
      (ii) (−)-carvone
      (iii) menthone and
      (iv) isomenthone
   wherein the 4-methyl-delta-hexylactone is employed in an amount which is sufficient to impart, modify and/or intensify one or more smell or flavour impressions and richness in said odoriferous or aroma substance composition, and
   where said 4-methyl-delta-hexylactone is present in an amount effective to impart the hay-like, coumaric note to said odoriferous or aroma substance composition and where said 4-methyl-delta-hexylactone by itself does not have a hay-like coumaric note.

10. The article according to claim 1, wherein said article does not contain a fraction or natural oil which by itself exhibits a hay-like, coumaric note.

11. A perfume or aroma composition according to claim 1, wherein said mixture has a hay-like, coumaric note and where a sweet, phenolic, chemical or fruity smell and flavor impression of said 4-methyl-delta-hexylactone is suppressed.

12. The composition of claim 11, wherein said 4-methyl-delta-hexylactone is included in an amount of 50 to 8,000 ppm based on the total amount of the composition.

13. A method for imparting, modifying and/or intensifying one or more smell or flavour impressions and richness in the mouth of a person comprising adding, mixing or contacting a product with a mixture comprising
(a) 4-methyl-delta-hexylactone, and
(b) at least one compound chosen from the group consisting of:
  (i) menthol,
  (ii) (−)-carvone
  (iii) menthone and
  (iv) isomenthone
  where the amount of said 4-methyl-delta-hexylactone imparts a hay-like, coumaric note to the product and where said 4-methyl-delta-hexylactone by itself does not have a hay-like, coumaric note,
and introducing the product containing the mixture to the mouth.

14. A formulation for nutrition, oral care or consumption for pleasure, comprising an article in the form of an odoriferous or aroma substance composition according to claim 2 in an amount of 0.05 to 50 wt. %, based on the total weight of said formulation.

* * * * *